(12) United States Patent
Crothers

(10) Patent No.: US 8,318,919 B2
(45) Date of Patent: Nov. 27, 2012

(54) NUCLEIC ACID HYBRIDIZATION METHODS

(75) Inventor: Donald M. Crothers, Northford, CT (US)

(73) Assignee: Geneohm Sciences, Inc., San Diego, CA (US)

(*) Notice: Subject to any disclaimer, the term of this patent is extended or adjusted under 35 U.S.C. 154(b) by 556 days.

(21) Appl. No.: 12/464,028

(22) Filed: May 11, 2009

(65) Prior Publication Data

US 2009/0227473 A1    Sep. 10, 2009

Related U.S. Application Data

(63) Continuation of application No. 10/996,621, filed on Nov. 10, 2004, now Pat. No. 7,531,306.

(60) Provisional application No. 60/519,568, filed on Nov. 12, 2003.

(51) Int. Cl.
C07H 21/04      (2006.01)
C12M 1/00       (2006.01)

(52) U.S. Cl. .................................. 536/24.3; 435/283.1

(58) Field of Classification Search .................. None
See application file for complete search history.

(56) References Cited

U.S. PATENT DOCUMENTS

| | | | |
|---|---|---|---|
| 5,137,814 A * | 8/1992 | Rashtchian et al. ........ 435/91.41 |
| 5,143,854 A | 9/1992 | Pirrung et al. | |
| 5,312,527 A | 5/1994 | Mikkelsen et al. | |
| 5,384,261 A | 1/1995 | Winkler et al. | |
| 5,412,087 A | 5/1995 | McGall et al. | |
| 5,512,439 A * | 4/1996 | Hornes et al. ................. 435/6.11 |
| 5,776,672 A | 7/1998 | Hashimoto et al. | |
| 5,807,522 A * | 9/1998 | Brown et al. ................... 422/50 |
| 5,871,918 A | 2/1999 | Thorp et al. | |
| 5,871,981 A | 2/1999 | Chartrain et al. | |
| 5,972,692 A | 10/1999 | Hashimoto et al. | |
| 6,200,761 B1 | 3/2001 | Meade et al. | |
| 6,221,586 B1 | 4/2001 | Barton et al. | |
| 6,291,187 B1 | 9/2001 | Kingsmore et al. | |
| 6,391,558 B1 | 5/2002 | Henkens et al. | |
| 7,531,306 B2 | 5/2009 | Crothers | |
| 2003/0104459 A1 | 6/2003 | Faham et al. | |
| 2005/0176035 A1 | 8/2005 | Crothers | |

FOREIGN PATENT DOCUMENTS

| | | |
|---|---|---|
| EP | 415755 A2 | 3/1991 |
| WO | WO 95/06753 | 3/1995 |
| WO | WO 9506753 A1 * | 3/1995 |
| WO | WO 97/19193 | 5/1997 |
| WO | WO 98/46793 | 10/1998 |
| WO | WO 01/06012 | 1/2001 |

OTHER PUBLICATIONS

Alper, "Drug Discovery on the Assembly Line" Science (1994) 264: 1399-1401.

Bains, "Characterizing and Sequencing cDNAs using Oligonucleotide Hybridization" J. DNA Seq. Map (1993) 4: 143-150.
Brenner, et al., "Encoded Combinatorial Chemistry" Proc. Natl. Acad. Sci. (1992) 89: 5381-5383.
Chen, et al., "Amplification of Closed Circular DNA in vitro" Nucleic Acids Research (1998) 26(23): 1126-1127.
Drmanac, et al., "DNA Sequence Determination by Hybridization: A Strategy for Efficient Large-Scale Sequencing" Science (1993) 260: 1649-1652.
Horn, et al., "An Improved Divergent Synthesis of Comb-Type Branched Oligodeoxyribonucleotides (bDNA) Containing Multiple Secondary Sequences" Nucleic Acids Res. (1997) 25(23): 4835-4841.
Keller, et al., DNA Probes, $2^{nd}$ Edition, Stockton Press, New York (1993).
Khudyakov, et al., "Primer Specific Solid-phase Detection of PCR Products" Nucleic Acids Research (1994) 22(7): 1320-1321.
Kunkel, "Rapid and Efficient Site-specific Mutagenesis without Phenotypic Selection" Proc. Natl. Acad. Sci. (1985) 82(2): 488-492.
Lizardi, et al. "Mutation Detection and Single-Molecule Counting Using Isothermal Rolling-Circle Amplification" Nature Genetics (1998) 19: 225-232.
Longo, et al., "Use of Uracil DNA Glycosylase to Control Carry-over Contamination in Polymerase Chain Reactions" Gene (1990) 93(1): 125-128.
Milligan, et al., "Current Concepts in Antisense Drug Design" J. Med. Chem. (1993) 36: 1923-1937.
Needels, et al., "Generation and Screening of an Oligonucleotide-encoded Synthetic Peptide Library" Proc. Nat. Acad. Sci. (1993) 90: 10700-10704.
Sambrook, et al., Molecular Cloning: A Laboratory Manual, $2^{nd}$ Edition, Cold Spring Harbor Laboratory, New York (1989).
Steele, et al., "Electrochemical Quantitation of DNA Immobilized on Gold" Anal. Chem. (1998) 70: 4670-4677.
Suyama, et al., "Gene Expression Analysis of DNA Computing" Curr. Comp. Mol. Biol. (2000) 7: 12-13.
Urdea, "Branched DNA Signal Amplification" Biotechnology (1994) 12: 926.
Supplementary Search Report cited in European Application No. EP 04 81 9073, issued on Jul. 3, 2008.
International Search Report and Written Opinion dated Mar. 30, 2007 for Application No. PCT/us2004/37472, filed Nov. 10, 2004.
European Office Action dated Mar. 7, 2011 for Application No. EP 04819073.0, filed Nov. 10, 2004.
Examination Report dated Jul. 30, 2012 for European Application No. 04819073.0 filed Nov. 10, 2004.

* cited by examiner

Primary Examiner — Christopher M. Babic
(74) Attorney, Agent, or Firm — Knobbe, Martens, Olson & Bear LLP

(57) ABSTRACT

Disclosed herein are methods of destabilizing double-stranded nucleic acid hybridization using an enzyme comprising DNA N-glycosylase activity. Also disclosed herein is the detection of a double-stranded target DNA wherein the hybridization of duplex strands has been at least partially disrupted thereby permitting invasion of a probe strand. Also disclosed herein are methods of using an enzyme comprising DNA N-glycosylase activity to generate single-stranded circular nucleic acids.

4 Claims, 11 Drawing Sheets

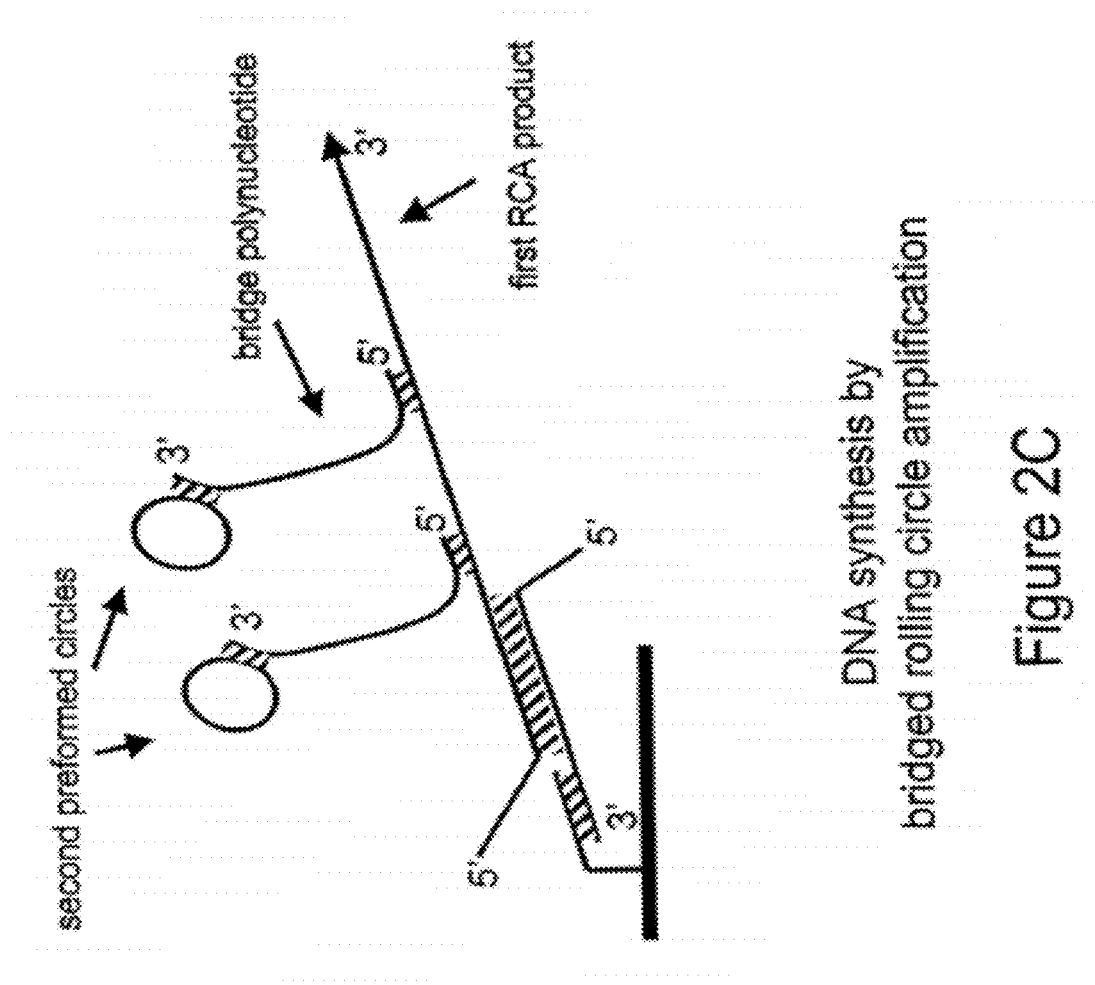

NUCLEIC ACID HYBRIDIZATION METHODS

RELATED APPLICATIONS

This application is a continuation and claims the benefit of priority of U.S. patent application Ser. No. 10/996,621, filed Nov. 10, 2004, now U.S. Pat. No. 7,531,306, which claims priority under 35 U.S.C. §119(e) to U.S. Provisional Patent Application No. 60/519,568, entitled NUCLEIC ACID HYBRIDIZATION METHODS, filed Nov. 12, 2003. These applications are incorporated herein by reference in its entirety.

REFERENCE TO SEQUENCE LISTING

The present application is being filed along with a Sequence Listing in electronic format. The Sequence Listing is provided as a file entitled GENOM040C1.TXT, created May 8, 2009, which is 1.71 KB in size. The information in the electronic format of the Sequence Listing is incorporated herein by reference in its entirety.

BACKGROUND OF THE INVENTION

1. Field of the Invention

The present invention relates to the field of nucleic acid hybridization. More specifically, some embodiments of the present invention relate to methods of locally destabilizing the hybridization between two nucleic acid molecules thereby providing a region of unpaired nucleic acids that is free to interact with other molecules.

2. Description of the Related Art

Hybridization of polynucleotides to other polynucleotides having at least a portion of complementary nucleotide sequence by Watson-Crick base pairing is a fundamental process useful in a wide variety of research, medical, and industrial applications. Detecting the hybridization of a probe to a polynucleotide containing a target sequence is useful for gene expression analysis, DNA sequencing, and genomic analysis. Particular uses include identification of disease-related polynucleotides in diagnostic assays, screening for novel target polynucleotides in a sample, identification of specific target polynucleotides in mixtures of polynucleotides, identification of variant sequences, genotyping, amplification of specific target polynucleotides, and therapeutic blocking of inappropriately expressed genes, e.g. as described in Sambrook et al., *Molecular Cloning: A Laboratory Manual*, 2$^{nd}$ Edition (Cold Spring Harbor Laboratory, New York, 1989); Keller and Manak, *DNA Probes*, 2$^{nd}$ Edition (Stockton Press, New York, 1993); Milligan et al., 1993, *J Med Chem*, 36: 1923-1937; Drmanac et al., 1993. *Science*, 260: 1649-1652; Bains, 1993, *J DNA Seq Map*, 4: 143-150.

Immobilized probes are useful for detecting polynucleotides containing a target nucleotide sequence, where each immobilized probe is functionally connected to a support and the hybridization of a polynucleotide to the immobilized probe can be detected. Most commonly, DNA probes are used to detect polynucleotides containing a target nucleotide sequence complementary to the probe sequence. The support for immobilized probes may be a flat surface, often called a "chip," or the support may be the surface of a bead or other particle. Probes are usually immobilized in a known arrangement, or array, which provides a medium for matching known and unknown polynucleotides based on base-pairing rules. Preferably, the process of identifying the unknowns identified using a probe array is automated. Microarrays having a large number of immobilized probes of known identity are used to determine complementary binding, allowing massively parallel studies of gene expression and gene discovery. For example, an experiment with a single DNA chip can provide researchers information on thousands of genes simultaneously. For example, Hashimoto et al. disclose an array of immobilized single-stranded probes wherein at least one probe has a nucleotide sequence complementary to the target gene(s) to be detected, such that each probe is immobilized onto the surface of an electrode or the tip of an optical fiber and an electrochemically or optically active substance capable of binding to double-stranded nucleic acid is used to detect hybridization of target genes to complementary immobilized probes (U.S. Pat. Nos. 5,776,672 and 5,972,692).

Universal Chips

Under some circumstances, a drawback to chip technology is that each chip must be manufactured specifically for the sequences to be detected, with a set of immobilized probes that are designed to be complementary to specific sequences to be detected. Chips specific for a single organism require a large manufacturing investment, and the chips can only be used for a narrowly defined range of samples. In contrast, a "universal chip" or "universal array" is organism-independent because the probes are not targeted to organism-specific sequences or products. Chips specific for a specific tissue, physiological condition, or developmental stage, often used for gene expression analysis, can likewise require a substantial manufacturing investment for use with a limited range of samples. A universal chip provides an unrestricted approach to studying tissues, physiological conditions, or developmental stages of interest. Manufacturing quality control can be improved by using a universal chip for polynucleotide detection.

One approach to universal chip design involves attaching a set of oligonucleotide probes to a chip surface, where the set of oligonucleotide probes includes all possible sequences of oligonucleotides that are 5, 6, 7, 8, 9, 10 or more nucleotides in length. The probes needed for these arrays can be designed using a simple combinatorial algorithm. The chip is incubated with a mixture that may contain DNA, cDNA, RNA or other hybridizable material, and hybridization to each probe of known sequence is measured. However, the specificity of such an array may be impaired because different sequences may have different requirements for stringent hybridization. In addition, such a universal array does not prevent false positives resulting from frameshifting where, for example in a universal array having probes that are six nucleotides long, the final four nucleotides of a sample polynucleotide may hybridize to the complementary final four nucleotides of a six-nucleotide probe, but the same sample polynucleotide would not hybridize to the entire six-nucleotide probe sequence.

Suyama et al. (2000, *Curr Comp Mol Biol* 7:12-13) disclose a universal chip system for gene expression profiling of a sample, where the chip system utilizes "DNA computing" instead of binding of transcripts to probes. The DNA computing system of Suyama et al. indirectly determines which transcripts are present by measuring binding of coded adapters to a universal set of immobilized probes on the universal chip. Only those coded adapters with a region complementary to a region of a transcript present in a sample will undergo the subsequent manipulations and the processing steps that generate adapters capable of binding to probes on the universal chip.

Tags

An alternative approach to manufacturing a universal chip involves using a set of tag sequences that do not naturally occur in the target polynucleotides, where the tags bind to complementary probes on a universal chip. Tags for such uses are sometimes known as "address tags" or "zip codes" or are considered to be analogous to "bar codes" for identifying targets. Detection, identification, tracking, sorting, retrieving or other manipulations are then directed at tag sequences and not the sequences of the target polynucleotides. Oligonucleotide tags may be covalently attached to or incorporated into polynucleotides. Tags may become associated with a polynucleotide by hybridization of a separate oligonucleotide which functions as a linker by virtue of having at least two domains, one with a tag sequence complementary to a probe and one with sequence complementary to at least a portion of the target polynucleotide. Systems employing oligonucleotide tags have been proposed as means for manipulating and identifying individual molecules in complex mixtures, for example to detect polynucleotides having target nucleotide sequences, or as an aid to screening genomic, cDNA, or combinatorial libraries for drug candidates. Brenner and Lerner, 1992, *Proc Nall Acad Sci,* 89: 5381-5383; Alper, 1994, *Science,* 264: 1399-1401; Needels et al., 1993, *Proc Nat Acad Sci,* 90: 10700-10704.

Many applications of chip technology involve PCR amplicons or other nucleic acids that are normally double stranded. A serious disadvantage exists, however, when using such double-stranded nucleic acids in certain chip-based applications. For example, when hybridizing one strand of a double-stranded nucleic acid to a surface, such hybridization must compete with rehybridization with the complementary strand in solution. One solution to this problem has been the use of "asymmetric PCR" to generate single-stranded nucleic acids. In "asymmetric PCR" the template nucleic acid is mixed with an excess of one primer over the other, thereby generating more of the desired strand than the undesired strand. This approach, however, limits the yield of the amplicon which becomes particularly acute in multiplexed applications. Another approach to ameliorating the competition problem is selective exonuclease digestion of the undesired strand. In these applications, however, the desired strand must be made exonuclease resistant. Generating these exonuclease resistant nucleic acids strands requires a more complex synthesis. Furthermore, long incubation times are required for exonuclease digestions. Accordingly, there exists a need for a fast simple method for reducing nucleic acid strand rehybridization that is sufficiently robust for use in multiplexing applications.

SUMMARY OF THE INVENTION

Some embodiments of the present invention are set out in the following numbered paragraphs.

1. A method of nucleic acid strand invasion, the method comprising:
    obtaining a double-stranded DNA comprising a first strand hybridized to a second strand, wherein the first strand comprises at least one non-natural DNA base;
    incubating the double-stranded DNA with an enzyme that removes the non-natural DNA base so as to destabilize hybridization between the first strand and the second strand, thereby generating an exposed region of the second strand; and
    contacting the exposed region of the second strand with a polynucleotide, which is complementary to at least a portion of the exposed region of the second strand, under conditions which permit hybridization of the polynucleotide to the second strand.

2. The method of 1, wherein the enzyme comprises a DNA N-glycosylase activity.

3. The method of 2, wherein the enzyme is uracil-DNA glycosylase.

4. The method of 1, wherein the enzyme comprises both a DNA N-glycosylase activity and an AP-lyase activity.

5. The method of 1, wherein the enzyme is selected from the group consisting of Fpg, hOGG1, endonuclease VIII and endonuclease III.

6. The method of 1 further comprising incubating the double-stranded DNA with an AP-endonuclease thereby partially degrading the first strand.

7. The method of 1, wherein the non-natural DNA base is selected from the group consisting of uracil, 7,8-dihydro-8-oxoguanine (8-oxoguanine), 8-oxoadenine, foramidopyrimidine (fapy)-guanine, methyl-fapy-guanine, fapy-adenine, aflatoxin $B_1$-fapy-guanine, 5-hydroxy-cytosine, 5-hydroxy-uracil, urea, 5,6-dihydroxythymine, thymine glycol, 5-hydroxy-5-methylhydanton, uracil glycol, 6-hydroxy-5,6-dihydrothymine and methyltartronylurea.

8. The method of 1, wherein the non-natural DNA base is uracil.

9. A method of nucleic acid strand invasion, the method comprising:
    obtaining a double-stranded DNA comprising a first strand hybridized to a second strand, wherein uracil replaces at least one thymine in the first strand;
    incubating the double-stranded DNA with uracil-DNA glycosylase so as to destabilize hybridization between the first strand and the second strand, thereby generating an exposed region of the second strand; and
    contacting the exposed region of the second strand with a polynucleotide, which is complementary to at least a portion of the exposed region of the second strand, under conditions which permit hybridization of the polynucleotide to the second strand.

10. The method of 9 further comprising incubating the double-stranded DNA with AP-endonuclease thereby partially degrading the first strand.

11. The method of 9 further comprising hydrolyzing the first strand by heating the double-stranded DNA.

12. The method of 9, wherein the double stranded DNA is circular.

13. The method of 12, wherein uracil replaces every thymine in the first strand.

14. The method of 13, wherein the first strand is hydrolyzed by heating the double-stranded DNA.

15. The method of 9, wherein the double-stranded DNA is linear.

16. The method of 15, wherein the first strand of the double-stranded DNA comprises a first 5' flap sequence.

17. The method of 16, wherein uracil replaces thymine only in the first 5' flap sequence.

18. The method of 16, wherein the exposed region of the second strand, which is complementary to the first 5' flap sequence, comprises a tag sequence.

19. The method of 18, wherein the first 5' flap sequence comprises a sequence complementary to the tag sequence.

20. The method of 19, wherein the tag sequence hybridizes with a capture probe.

21. The method of 15, further comprising contacting the exposed region of the second strand with a primer for head-to-tail hybridization.

22. The method of 15, further comprising contacting the exposed region of the second strand with a circular RCA template.

23. The method of 15, further comprising contacting the exposed region of the second strand with a polynucleotide conjugated to a detector molecule.

24. The method of 23, wherein the detector molecule is a redox enzyme.

25. The method of 23, wherein the detector molecule is an antibody-horse radish peroxidase complex.

26. The method of 15, wherein the first strand of the double-stranded DNA comprises a first 5' flap sequence and wherein, the second strand of the double-stranded DNA comprises a second 5' flap sequence.

27. The method of 26, wherein uracil replaces thymine in the first 5' flap sequence and in the second 5' flap sequence.

28. The method of 27, wherein the region of the first strand that is complementary to the second 5' flap sequence becomes exposed after incubation of the double-stranded DNA with uracil-DNA glycosylase.

29. The method of 28, further comprising:
contacting the exposed region on the second strand with a capture probe; and
contacting the exposed region on the first strand with a polynucleotide selected from the group consisting of a primer for head-to-tail hybridization, a circular RCA template and a polynucleotide conjugated to a detector molecule.

30. The method of 29, wherein the detector molecule is a redox enzyme.

31. The method of 29, wherein the detector molecule is an antibody-horse radish peroxidase complex.

32. A method of detecting a target DNA, the method comprising:
obtaining a double-stranded target DNA comprising a first strand hybridized to a second strand, wherein uracil replaces at least one thymine is the first strand;
incubating the double-stranded target DNA with uracil-DNA glycosylase so as to destabilize hybridization between the first strand and the second strand, thereby generating an exposed region of the second strand;
contacting the second strand with a capture probe, which is complementary to at least a portion of the exposed region of the second strand, under conditions which permit hybridization of the capture probe to the second strand; and
detecting the target DNA by determining whether a signal indicative of the presence of the target DNA has been generated.

33. The method of 32 further comprising incubating the double-stranded target DNA with AP-endonuclease thereby partially degrading the first strand.

34. The method of 32 further comprising hydrolyzing the first strand by heating the double-stranded target DNA.

35. The method of 32, wherein the double stranded DNA is circular.

36. The method of 32, wherein the capture probe is coupled to a detection zone.

37. The method of 36, wherein the detection zone is an electrode.

38. The method of 32, wherein the double-stranded target DNA is linear.

39. The method of 38, wherein the first strand of the double-stranded target DNA comprises a first 5' flap sequence.

40. The method of 39, wherein uracil replaces thymine only in the first 5' flap sequence.

41. The method of 39, wherein the exposed region of the second strand, which is complementary to the first 5' flap sequence, comprises a tag sequence.

42. The method of 41, wherein the first 5' flap sequence comprises a sequence complementary to the tag sequence.

43. The method of 41, wherein the tag sequence hybridizes with the capture probe.

44. The method of 38, wherein the first strand of the double-stranded DNA comprises a first 5' flap sequence and wherein, the second strand of the double-stranded DNA comprises a second 5' flap sequence.

45. The method of 44, wherein uracil replaces thymine in the first 5' flap sequence and in the second 5' flap sequence.

46. The method of 45, wherein the region of the first strand that is complementary to the second 5' flap sequence becomes exposed after incubation of the double-stranded DNA with uracil-DNA glycosylase.

47. The method of 46, further comprising contacting the exposed region of the first strand with a primer for head-to-tail hybridization.

48. The method of 46, further comprising contacting the exposed region of the first strand with a circular RCA template.

49. The method of 46, further comprising contacting the exposed region of the first strand with a polynucleotide conjugated to a detector molecule.

50. The method of 49, wherein the detector molecule is a redox enzyme.

51. The method of 49, wherein the detector molecule is an antibody-horse radish peroxidase complex.

52. A method of forming a single stranded circular DNA, the method comprising:
obtaining a linear single-stranded DNA comprising a 5' annealing sequence and a 3' annealing sequence;
hybridizing the linear single-stranded DNA with a probe DNA having a first sequence complementary to the 5' annealing sequence adjacent a second sequence complementary to the 3' annealing sequence, wherein uracil replaces at least one thymine in the first and second complementary sequences;
ligating the 5'-end of the linear single-stranded DNA to the 3'-end of the linear single-stranded DNA, thereby forming a single-stranded circular DNA hybridized to the probe DNA; and
incubating the probe DNA with uracil-DNA glycosylase, thereby destabilizing the hybridization between the single-stranded circular DNA and the probe DNA.

53. The method of 52, further comprising hydrolyzing the probe DNA with heat.

54. The method of 52, wherein the single-stranded circular DNA comprises a tag sequence.

55. The method of 54, wherein the tag sequence is complementary to a capture probe.

56. The method of 55 further comprising contacting the single-stranded circular DNA with the capture probe under conditions which permit hybridization of the single-stranded circular DNA to the capture probe.

57. A kit comprising:
an enzyme comprising DNA N-glycosylase activity; and
instructions for using the enzyme to destabilize hybridization between two DNA strands.

58. The kit of 57 further comprising AP-endonuclease.

59. The kit of 58 further comprising a chip comprising a plurality of capture probes.

60. The kit of 59 further comprising one or more primers complementary to at least a portion of a desired target DNA.

61. The kit of 57, wherein the enzyme is uracil DNA-glycosylase.

62. A mixture comprising a first double stranded DNA, which comprises a portion in which hybridization between a first strand and a second strand has been destabilized by removing at least one non-natural DNA base, thereby generating an exposed region of the second strand, and a second DNA which is hybridized to the exposed region of the second strand.

63. The method of 62, wherein the non-natural DNA base is selected from the group consisting of uracil, 7,8-dihydro-8-oxoguanine (8-oxoguanine), 8-oxoadenine, foramidopyrimidine (fapy)-guanine, methyl-fapy-guanine, fapy-adenine, aflatoxin $B_1$-fapy-guanine, 5-hydroxy-cytosine, 5-hydroxy-uracil, urea, 5,6-dihydroxythymine, thymine glycol, 5-hydroxy-5-methylhydanton, uracil glycol, 6-hydroxy-5,6-dihydrothymine and methyltartronylurea.

64. The method of 62, wherein the non-natural DNA base is uracil.

BRIEF DESCRIPTION OF THE DRAWINGS

FIG. 2C illustrates destabilization of hybridization in regions at the ends of a linear double-stranded DNA using uracil-DNA glycosylase, subsequent hybridization of one end to a surface and extension of the other end by branched RCA.

DETAILED DESCRIPTION OF THE PREFERRED EMBODIMENT

Figure 1:
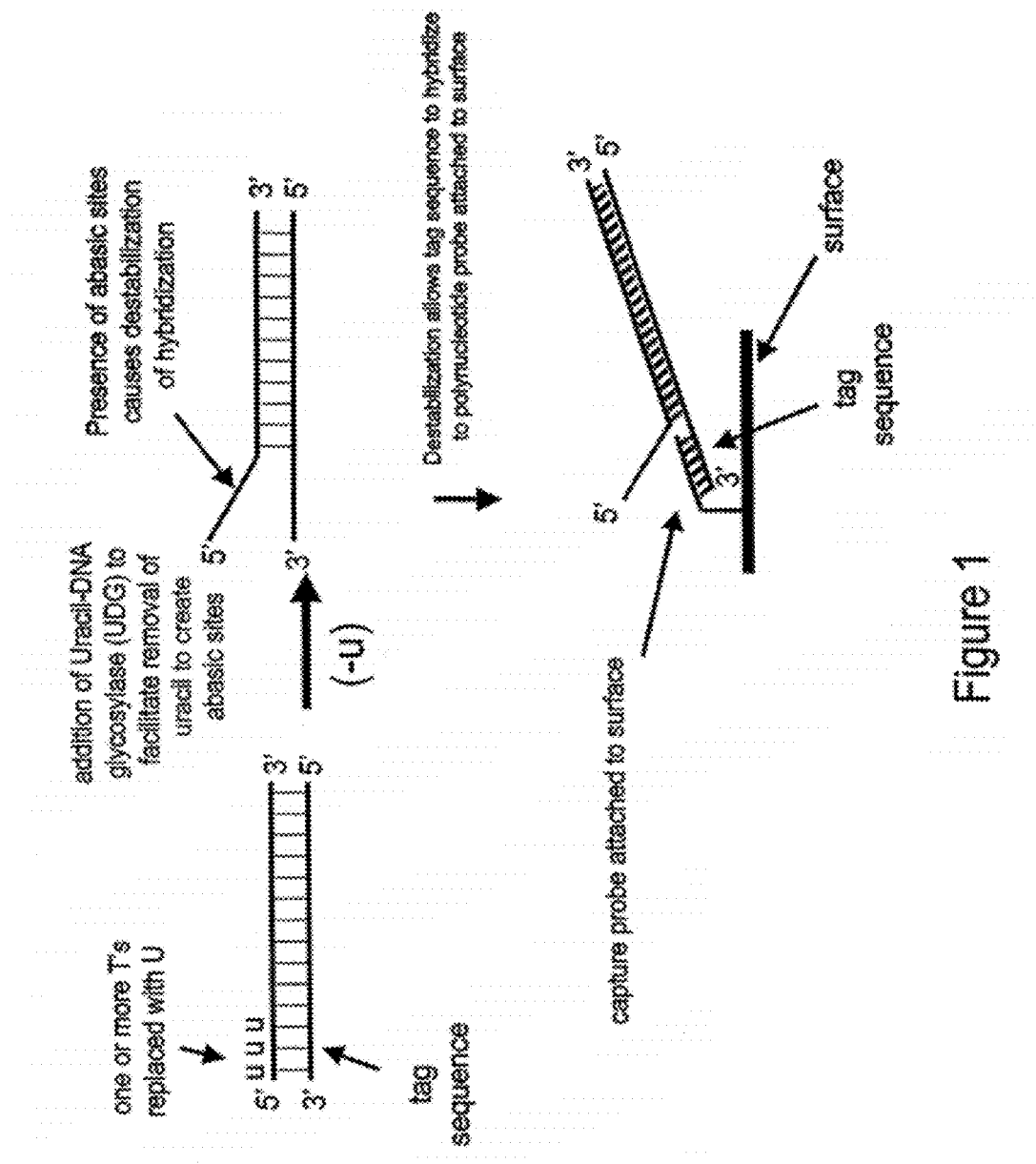
FIG. 1 illustrates destabilization of hybridization in a region of a double-stranded DNA using uracil-DNA glycosylase and subsequent hybridization to a probe coupled to a surface.

Some embodiments of the present invention relate to methods of destabilizing the hybridization between two strands of a double-stranded DNA molecule. In some embodiments, hybridization can be destabilized such that the two DNA strands become entirely separated. In other embodiments, only a pre-selected, localized region of the duplex DNA is targeted for destabilization. Using the methods described herein, destabilization of hybridization results in strand separation that permits one of the strands of the DNA duplex to be used in subsequent hybridizations while reducing the ability of the other strand of the duplex DNA to hybridize, thereby reducing the interference from competing rehybridization.

Some embodiments of the present invention relate to methods for detecting a double-stranded target DNA. Methods described herein are used to destabilize hybridization in preselected regions of the duplex DNAs thereby generating at least one exposed single-stranded region that can be used to attach the target DNA to a surface such as a chip. Additional exposed single-stranded regions can be generated thus allowing for hybridization with polynucleotide probes and/or other molecules which are involved in signal amplification and/or signal generation.

Other embodiments of the present invention relate to methods for generating a single-stranded circular DNA molecule by hybridizing a single-stranded linear DNA strand with a single-stranded template DNA, joining the ends of the linear strand by ligation, and destabilizing the hybridization between the resulting circular DNA and the template DNA.
Methods of Destabilizing Hybridization Between Two DNA Strands Numerous methods for destabilizing the hybridization between two nucleic acid strands are well known in the art. For example, heating a nucleic acid duplex thereby disrupting the hydrogen bonding between base pairs is one of the most common ways to facilitate the melting of a nucleic acid duplex. However, when the objective is to hybridize one of the duplex strands to a surface or to a specific probe, this method is disadvantageous because of the competition with rehybridization with the complementary duplex strand in solution. The destabilization methods described herein permit selective hybridization of one strand of the duplex DNA to an exogenous polynucleotide while reducing the ability of the other strand of the duplex DNA to form hybrids. By "exogenous polynucleotide" is meant any polynucleotide that is not a part of the double-stranded DNA molecule prior to hybridization. Exogenous polynucleotides can include, but are not limited to, sequence specific capture probes, capture probes comprising one or more sequences complementary to an address tag, capture probes coupled to detectors, probes comprising amplification tags, probes comprising detection tags, probes comprising identifier tags, probes comprising a combination of tags, detection probes, and signal generating probes. Additionally, exogenous polynucleotides can include modified bases, non-naturally occurring bases, labels, ligands and/or other materials and modifications suitable to a particular application. Exogenous polynucleotides can be directly synthesized or generated from any suitable template including but not limited to genomic DNA, cDNA, PCR products, LCR products, RCA amplification products, synthetic DNA, other forms of DNA, mRNA, rRNA, synthetic RNA, and other forms of RNA.

In general, capture probes are probes that are attached to a surface or another molecule. Capture probes can be specific for one or a limited number of complementary nucleic acid sequences. Alternatively, capture probes can comprise one or more sequences complementary to universal tag sequences (address tags) which are present in a set of nucleic acids of interest. Such capture probes will bind to nucleic acids which comprise the corresponding (complementary) address tag sequence.

A capture probe can also be coupled to a detector. In such embodiments, a capture probe can be used to determine whether a nucleic acid comprising a sequence complementary to at least a portion of the capture probe sequence is present in a sample. For example, a capture probe can be coupled directly to a detector molecule or otherwise coupled to a detection zone that is present on a surface.

As used herein, "amplification tag" means a nucleotide sequence that is recognized by a probe or other molecule that is used in the generation of a polynucleotide sequence coupled to a target DNA molecule. For example, molecules such as a head-to-tail probe or an RCA template can bind to an amplification tag. In some embodiments of the present invention, an amplification tag can be incorporated directly into a target DNA. In other embodiments, amplification tags are incorporated into a nucleic acid probe that can hybridize with a target nucleic acid.

As used herein, "detection tag" means a nucleic acid sequence that is complementary to at least a portion of a detection probe or a signal generating probe.

As used herein, a "detection probe" is a probe which comprises a sequence that is complementary to a detection tag and which directly or indirectly provides a signal indicative of the presence of a target nucleic acid. A detection probe can also comprise a detector molecule. A detector molecule can be a ligand for an antibody or other binding molecule. Additionally, a detector molecule can be a charged or uncharged molecule which binds to DNA or a molecule which actively generates a signal, such as a redox enzyme. A detector molecule can, but need not, be used in connection with a detection probe. A detection probe having a signal generating molecule coupled thereto is also known as a signal generating probe. A signal generating molecule actively generates a signal.

As used herein, "identifier tag" means a nucleic acid sequence that is used to identify a target DNA or other nucleic acid of interest. Thus, nucleic acid sequences which comprise an identifier tag will hybridize with a probe having a nucleotide sequence complementary to the identifier tag.

Some embodiments of the present invention are related to destabilization of a DNA duplex which includes one or more non-natural DNA bases. By "non-natural DNA base" is meant any base that it not one of the four bases commonly found in DNA. The four commonly found bases include, and are limited to, adenine (A), guanine (G), thymine (T) and cytosine (C). Non-natural bases include, but are not limited to, uracil, 7,8-dihydro-8-oxoguanine (8-oxoguanine), 8-oxoadenine, foramidopyrimidine (fapy)-guanine, methyl-fapy-guanine, fapy-adenine, aflatoxin $B_1$-fapy-guanine, 5-hydroxy-cytosine, 5-hydroxy-uracil, urea, 5,6-dihydroxythymine, thymine glycol, 5-hydroxy-5-methylhydanton, uracil glycol, 6-hydroxy-5,6-dihydrothymine and methyltartronylurea. Non-natural DNA bases are included in the double-stranded DNA so that many or all of these bases can form hydrogen bonds with the DNA bases paired across from them. Accordingly, the double-stranded DNA comprising one or more non-natural DNA bases forms a stable duplex. Hybridization of such duplex DNA can be destabilized as desired by adding one or more enzymes comprising a DNA N-glycosylase activity which remove the non-natural DNA bases. In some embodiments, non-natural DNA bases are included throughout one or both strands of the DNA duplex such that incubation with one or more enzymes comprising a DNA N-glycosylase activity destabilizes hybridization of the entire DNA duplex. In other embodiments, non-natural DNA bases are included in localized regions of one or both strands of the DNA duplex such that incubation with one or more enzymes comprising a DNA N-glycosylase activity destabilizes hybridization of only the localized regions.

One or more non-natural DNA bases can be included in a DNA duplex molecule using a number of methods known in the art. For example, DNA strands which comprise at least one non-natural DNA base can be generated by direct synthesis or any primer mediated DNA synthesis methods. One method of generating a DNA duplex comprising at least one non-natural DNA base in one or both strands of a duplex DNA molecule is to design primers which have been synthesized using non-natural DNA phosphoramidites in place of one or more of the natural DNA phosphoramidites. Such primers are then used in DNA amplification methods including, but not limited to, polymerase chain reaction (PCR), ligase chain reaction (LCR) and rolling circle amplification (RCA).

The destabilization methods described herein can be used with any double-stranded or partially double-stranded DNA that includes at least one non-natural DNA base that can be recognized and specifically removed using one or more enzymes. In some embodiments of the present invention, the enzyme which recognizes and specifically removes non-natural DNA bases is an enzyme which comprises a DNA N-glycosylase activity. DNA N-glycosylases are enzymes that specifically recognize one or a set of non-natural DNA bases and remove them from a DNA duplex by cleaving the bond between C1' of the deoxyribose sugar and N1 of the non-natural DNA base, thereby leaving an abasic site. If the removed non-natural DNA base is a pyrimidine, then the abasic site that is generated is an apyrimidinic site. If the removed non-natural DNA base is a purine, then the abasic site that is generated is an apurinic site. Apyrimidinic sites and apurinic sites are generally referred to as AP sites. In some embodiments of the present invention, removal of one or more non-natural DNA bases in a region of a hybridized DNA duplex disrupts hydrogen bonding at the AP sites, thereby leading to destabilization of hybridization.

In some embodiments of the present invention, an enzyme comprising a DNA N-glycosylase activity also comprises a DNA AP-lyase (AP-lyase) activity. In other embodiments, the enzyme does not comprise an additional AP-lyase activity. AP-lyase is an enzyme which cleaves the bond between the sugar-phosphate backbone 3' to the AP site. The cleavage occurs between the 3' C and O of the deoxyribose sugar such that no 3' OH is available to prime DNA strand synthesis from the AP site. Some AP-lyases additionally cleave 5' of the AP site between the 3' C and O of the deoxyribose sugar immediately upstream of the AP site.

A number of enzymes which comprise a DNA N-glycosylase activity or both a DNA N-glycosylase activity and an AP-lyase activity are known in the art. A non-comprehensive description of some of the more common of these enzymes is provided herein. For example, some embodiments of the present invention utilize uracil DNA glycosylase (UDG) to destabilize DNA duplex hybridization by removing one or more non-natural DNA bases from the duplex DNA. Uracil DNA glycosylase is an enzyme which possesses DNA N-glycosylase activity but not an AP-lyase activity. Uracil DNA glycosylase specifically recognizes uracils that are present in DNA and cleaves the carbon-nitrogen bond leaving an apyrimidinic site.

In other embodiments, the enzyme hOGG1 is used to destabilize DNA duplex hybridization by removing one or more non-natural DNA bases. hOGG1 is an 8-oxoguanine DNA glycosylase which acts both as a N-glycosylase and an AP-lyase. The N-glycosylase activity releases certain non-natural purines from double stranded DNA, generating an apurinic site. The AP-lyase activity cleaves 3' to the AP site leaving a 5' phosphate and a 3' ring opened sugar. Some of the non-natural bases recognized and removed by hOGG1 include 7,8-dihydro-8-oxoguanine (8-oxoguanine) when base paired with cytosine, 8-oxoadenine when base paired with cytosine, foramidopyrimidine (fapy)-guanine and methyl-fapy-guanine.

Other embodiments of the present invention employ Fpg (formamidopyrimidine [fapy]-DNA glycosylase—also known as 8-oxoguanine DNA glycosylase) to destabilize hybridization by removing one or more non-natural DNA bases from duplex DNA. Fpg acts both as a N-glycosylase and an AP-lyase. The N-glycosylase activity releases non-natural purines from double stranded DNA, thereby generating an apurinic site. The AP-lyase activity cleaves both 3' and 5' to the AP site thereby removing the AP site and leaving a one base gap. Some of the non-natural bases recognized and removed by Fpg include 7,8-dihydro-8-oxoguanine (8-oxoguanine), 8-oxoadenine, fapy-guanine, methyl-fapy-guanine, fapy-adenine, aflatoxin $B_1$-fapy-guanine, 5-hydroxy-cytosine and 5-hydroxy-uracil.

In some embodiments of the present invention, endonuclease III (Nth) is used destabilize DNA duplex hybridization by removing one or more non-natural DNA bases. Endonuclease III acts both as a N-glycosylase and an AP-lyase. The N-glycosylase activity releases non-natural pyrimidines from double-stranded DNA, generating an apyrimidinic site. The AP-lyase activity of the enzyme cleaves 3' to the AP site leaving a 5' phosphate and a 3' ring opened sugar. Some of the non-natural bases recognized and removed by endonuclease III include urea, 5,6-dihydroxythymine, thymine glycol, 5-hydroxy-5-methylhydanton, uracil glycol, 6-hydroxy-5,6-dihydrothymine and methyltartronylurea.

In still other embodiments of the present invention, endonuclease VIII is used destabilize DNA duplex hybridization by removing one or more non-natural DNA bases. Endonuclease VIII acts as both an N-glycosylase and an AP-lyase. The N-glycosylase activity releases non-natural pyrimidines from double-stranded DNA, generating an apyrimidinic site. The AP-lyase activity cleaves 3' to the AP site leaving a 5' phosphate and a 3' ring opened sugar. Some of the non-natural bases recognized and removed by endonuclease VIII include urea, 5,6-dihydroxythymine, thymine glycol, 5-hydroxy-5-methylhydanton, uracil glycol, 6-hydroxy-5,6-dihydrothymine and methyltartronylurea.

In some embodiments of the present invention, a plurality of different enzymes comprising a DNA N-glycosylase activity or both a DNA N-glycosylase activity and an AP-lyase activity can be used to destabilize the hybridization of duplex DNA. In such embodiments, the duplex DNA can be incubated together with all of the enzymes or with each enzyme separately.

It will be appreciated that other enzymes, not specifically described herein, but which comprise a DNA N-glycosylase activity or both a DNA N-glycosylase activity and a DNA lyase activity, can be used in the methods and with the compositions described herein.

In some embodiments of the present invention, destabilization of hybridization can be further facilitated by limited hydrolysis of the strand containing one or more AP-sites by heating or by incubating the DNA with an AP-endonuclease. By "AP-endonuclease" is meant an enzyme comprising apyrimidinic endonuclease activity, an enzyme comprising apurinic endonuclease activity or and enzyme comprising both apyrimidinic and apurinic endonuclease activities.

All DNA molecules which comprise at least one non-natural DNA base are suitable for use in the destabilization methods described herein. In some embodiments, the double-stranded DNAs are completely synthetic. In other embodiments, the double-stranded DNAs include, but are not limited to, copies of a target nucleic acid such as a gene or portion thereof, or an RNA or portion thereof.

Some applications of the duplex destabilization methods generally described above are further described below using a system based on the enzyme uracil-DNA glycosylase. In this system, one or more naturally occurring thymines in the DNA molecule are replaced with uracil, a base which does not naturally occur in DNA. Although these embodiments of the invention are described with respect to the uracil-DNA glycosylase system, it will be appreciated that these embodiments can be implemented using any of the enzymes and non-natural DNA bases described herein as well as other enzymes and non-natural DNA bases which function together in a manner as described herein.

Some of the methods of the present invention relate to destabilization of DNA duplexes comprising a first DNA strand and a second DNA wherein uracil replaces at least one of the thymine bases in the first strand. In some embodiments, uracil replaces several or all of the thymine bases in the first strand. DNA strands which contain uracil in place of thymine can be generated by direct synthesis or any primer mediated DNA synthesis methods. In some embodiments of the present invention, thymine to uracil replacements in one or both strands of a duplex DNA molecule are generated by designing primers which have been synthesized using deoxyuracil phosphoramidites in place of one or more deoxythymine phosphoramidites. Such primers are then used in DNA amplification methods including, but not limited to, polymerase chain reaction (PCR), ligase chain reaction (LCR) and rolling circle amplification (RCA).

In some embodiments of the present invention, PCR is used to generate the double-stranded DNA that is to be destabilized using the methods described herein. In some of these PCR-related embodiments, the first strand primer is synthesized such that uracil replaces at least one thymine. In other embodiments, uracil replaces each of the thymines in the first strand primer. The resulting PCR product comprises a first DNA strand having uracil in place of at least one thymine incorporated into its 5' region. The uracil-containing 5' region of the first strand is derived from the uracil-containing first strand primer DNA. In other embodiments, both the first strand primer and the second strand primer are synthesized such that uracil replaces at least one thymine in each of the primers. In other embodiments, uracil replaces each of the thymines in the first strand primer and each of the thymines in the second strand primer. The resulting PCR product comprises a first DNA strand hybridized to a second DNA strand wherein both DNA strands have uracil in place of at least one thymine incorporated into their 5' regions. In the case of the first strand, the 5' uracil(s) derives from the first strand primer. In the case of the second strand, the 5' uracil(s) derives from the second strand primer.

Double-stranded DNAs that comprise a strand having one or more uracils in place of thymines are targets for the destabilization of strand hybridization. In some embodiments of the present invention, strand destabilization is mediated by incubating the double-stranded DNA with uracil-DNA glycosylase (UDG).

Uracil-DNA glycosylase is a DNA repair enzyme that is normally responsible for removing uracil from DNA. Uracil can spontaneously arise in DNA due to the deamination of cytosine. Because cytosine normally pairs with guanine and uracil pairs with adenine, a change from cytosine to uracil would lead to a guanine to adenine transition upon DNA replication. Removal of uracil from DNA by uracil-DNA glycosylase initiates a repair process which restores cytosine at its original position. In particular, uracil-DNA glycosylase cleaves uracil from the DNA backbone by hydrolyzing the bond between the N1 nitrogen of uracil and C1' carbon of deoxyribose, thereby generating an apyrimidinic site. Following this cleavage, AP-endonuclease recognizes the abasic site and removes a short region of DNA around this site. Finally, a repair tract of DNA is synthesized using the 3' hydroxyl upstream of the apyrimidinic site as a primer for repair patch synthesis mediated by DNA polymerase.

In some embodiments of the present invention, the hybridization of the strands of double-stranded DNAs is destabilized by removing uracils from one or both of the strands using the enzyme uracil-DNA glycosylase. Removal of the uracils from the DNA strand decreases the stability of duplex formation by decreasing the number of hydrogen bonds present per unit length of the DNA duplex. If the region to be destabilized is short, only one or a few uracils need be present to completely destabilize hybridization. In one embodiment of the present invention, hybridization of the double stranded DNA can be completely destabilized using uracil-DNA glycosylase. In another embodiment, the destabilization of hybridization between the two DNA strands results in a preselected, localized region of destabilization. For example, a double-stranded PCR product can be generated using a first strand primer having uracil in place of at least one thymine. The PCR product is then incubated with uracil-DNA glycosylase thereby removing the uracils from the region of the first strand of each duplex DNA molecule that is derived from the first PCR primer. The removal of uracil creates apyrimidinic sites across from adenine residues on the complementary strand (second strand). The lack of hydrogen bonding at these positions destabilizes the hybridization of the apyrimidinic region of the first strand (the portion of the first strand derived from the first strand primer) with its complementary region. In some embodiments, the destabilized first strand region, which does not hybridize with the second strand, is present as a non-hybridized 5' flap sequence. The exposed (non-hybridized) region of the second strand that is complementary to the 5' flap sequence is available for hybridization with an exogenous polynucleotide. Because rehybridization of the 5' flap sequence with the second (complementary) strand is energetically unfavorable, in some embodiments, such rehybridization does not significantly interfere with the hybridization of the exposed region of the second strand with an exogenous polynucleotide that comprises a nucleotide sequence complementary to at least a portion of the exposed region of the second strand.

In another embodiment of the present invention, the destabilization of hybridization between the two DNA strands results in multiple pre-selected, localized regions of destabilization. Localized destabilization in multiple regions results in multiple exposed regions complementary to the abasic region which can be used for the hybridization of exogenous polynucleotides. In some embodiments, the exposed regions that are complementary to the abasic regions are all on the same strand of the double-stranded DNA. In an alternative embodiment, the exposed regions that are complementary to the abasic regions are on both strands of the double-stranded DNA. For example, a double-stranded PCR product can be generated using a first strand primer and a second strand primer, each of which have uracil in place of at least one thymine. The PCR product is then incubated with uracil-DNA glycosylase. The uracil-DNA glycosylase treatment removes the uracils from the region of the first strand of each duplex DNA molecule that is derived from the first PCR primer. Additionally, this treatment removes the uracils from the region of the second strand of each duplex DNA molecule that is derived from the second PCR primer. The reduction in hydrogen bonding at the apyrimidinic positions destabilizes the hybridization of the apyrimidinic regions of the first strand and the second strand (the portions of the first strand and the second strand derived from the first strand and second strand primers, respectively) with their complementary regions. In some embodiments, the destabilized first strand region, which does not hybridize with the second strand, is present as a non-hybridized first 5' flap sequence. Similarly, the destabilized second strand region, which does not hybridize with the first strand, is present as a non-hybridized second 5' flap sequence. The exposed (non-hybridized) regions of the first and second strands that are complementary to the second and first 5' flap sequences, respectively, are each available for hybridization with an exogenous polynucleotide. Because rehybridization of the first and second 5' flap sequences with their complementary strands is energetically unfavorable, in some embodiments, such rehybridization does not significantly interfere with the hybridization of the exposed regions with exogenous polynucleotides that comprises a nucleotide sequence complementary to at least a portion of the exposed region of said first or second strand.

In addition to destabilizing hybridization, formation of abasic sites in a strand of double-stranded DNA also confers sensitivity to strand degradation. For example, a strand comprising one or more abasic sites is subject to hydrolysis by heating. Additionally, a DNA strand which comprises one or more abasic sites is subject to endonucleolytic degradation using an AP-endonuclease (apyrimidinic or apurinic endonuclease) as appropriate. Some embodiments of the present invention contemplate strand hydrolysis subsequent to the removal of uracils. For example, any single-stranded region of DNA comprising one or more apyrimidinic sites, for example, a 5' flap sequence, can be hydrolyzed by heating. Alternatively, single-stranded regions comprising apyrimidinic sites can be degraded by incubation with AP-endonuclease.

Target DNA

In some embodiments of the present invention, the double-stranded DNA represents a target DNA. Some embodiments relate to the detection of such double-stranded target DNA molecules. Other embodiments relate to the detection of the presence of the target DNA molecule in a sample, such as a biological sample or a synthetic DNA sample. Still other embodiments of the present invention relate to the detection of target DNA molecules bound to a surface such as a chip.

DNA Chips

A term for a collection of probes in a known arrangement is an "array." An array of capture probes as disclosed herein provides a medium for detecting the presence of targets in a sample based on rules for nucleic acid hybridization. Generally, an array of capture probes refers to an array of probes immobilized to a support, where the sequence (the identity) of each capture probe at each location is known. Alternately, an array of capture probes may refer to a set of capture probes that are not immobilized and can be moved on a surface, or may refer to a set of probes coupled to one or more particles such as beads. In some embodiments, the process of detecting target DNAs hybridized to capture probes is automated. Microarrays having a large of number of immobilized capture probes of known identity can be used for massively parallel gene expression and gene discovery studies. A variety of detection methods for measuring hybridization of detector molecules are known in the art, including fluorescent, colorimetric, radiometric, electrical, or electrochemical means.

Diverse methods of making oligonucleotide arrays are known, for example as disclosed in U.S. Pat. Nos. 5,412,087, 5,143,854, and 5,384,261 (the disclosures of which are incorporated herein by reference in their entireties) and accordingly no attempt is made to describe or catalogue all known methods. In some embodiments of the present invention, arrays of capture probes are set out on the surface of a chip. Some chips can contain an array of gene-specific capture probes for hybridization with select nucleic acid sequences. Universal chips can contain an array of capture probes that comprise one or more sequences for use in capturing nucleic acids that comprise an address tag or an identifier tag (for universal tag assay).

One aspect of the present invention provides a universal chip having capture probes attached to a support that functions as an electrical contact surface or electrode to detect nucleic acid hybridization. Methods for attaching oligonucleotides to an electrical contact surface are well known, for example as disclosed in any of U.S. Pat. Nos. 5,312,527, 5,776,672, 5,972,692, 6,200,761, and 6,221,586, the disclosures of which are incorporated herein by reference in their entireties.

In the fabrication process, many other alternative materials and processes can be used. The substrate may be glass or other ceramic material; the bottom silicon dioxide can be replaced by silicon nitride, silicon dioxide deposited by other means, or other polymer materials; the conducting layer can be any appropriate material such as platinum, palladium, rhodium, a carbon composition, an oxide, or a semiconductor. For amperometric measurement either a three-electrode system consisting of a working electrode, counter electrode and reference electrode or a two-electrode system comprising a working and a counter/reference electrode is necessary to facilitate the measurement. The working electrodes should provide a consistent surface, reproducible response from the redox species of interest, and a low background current over the potential range required for the measurement. The working electrodes may be any suitable conductive materials, preferably noble metals such as gold and platinum, or conductive carbon materials in various forms including graphite, glassy carbon and carbon paste. For a three electrode system the reference electrode is usually silver or silver/silver chloride, and the counter electrode may be prepared by any suitable materials such as noble metals, other metals such as copper and zinc, metal oxides or carbon compositions. Alternatively, the conducting layer can be prepared by screen printing of the electrode materials onto the substrate. Screen printing typically involves preparation of an organic slurry or inorganic slurry of an electrode material, such as a fine powder of carbon or gold, onto the substrate through a silk screen. The electrode material slurry may be fixed on the surface by heating or by air drying. The electrode may be any suitable conductive material such as gold, carbon, platinum, palladium, indium-tin-oxide. It is often advantageous to coat the electrode surface with a material such as avidin, streptavidin, neutravidin, or other polymers, to increase the immobilization of capture probes. Methods for the attachment include passive adsorption and covalent attachment.

If gold is chosen for the conducting layer, the layer can be evaporated, sputtered, or electroplated. A low temperature oxide layer can be replaced by spin-on dielectric materials or other polymer materials such as polyimide, or parylene. Reagent and electrical connections can be on the same side of a chip or on adjacent sides, though the opposite side configuration is preferred. Materials, temperatures, times, and dimensions may be altered to produce detectors, preferably chips, having substantially the same properties and functionality, as will be appreciated by those of skill in the art. Materials, temperatures, times, and dimensions may be altered by one of skill in the art to produce chips having the properties desired for any particular embodiment.

As related to some aspects of the present invention, the capture probes are immobilized on a support having an array of electrodes sandwiched between two layers of silicon dioxide insulator attached to the silicon substrate, where a supporting layer is opposite the silicon substrate and the chip is oriented such that the silicon substrate is on the top and the supporting layer is on the bottom, as disclosed in U.S. patent application Ser. No. 10/121,240, METHOD FOR MAKING A MOLECULARLY SMOOTH SURFACE, filed Apr. 10, 2002, the disclosure of which is incorporated herein by reference in its entirety. In some embodiments, gold electrodes are used. Alternatively, carbon electrodes such as graphite, glassy carbon, and carbon paste can be used. In this embodiment, access to the surfaces of the working electrodes, where the capture probes are immobilized, is through windows through the silicon substrate and top layer of insulator on the top surface of the chip. Windows on the underside (etched through the supporting layer and the bottom layer of insulator) allow access to a counter (or detector) electrode and a reference electrode. For gold electrodes, the two types of electrodes in the chip are selectively interconnected by deposited gold wiring within the insulating layer or by other methods known in the art. Access to the working electrode, reference electrode, and counter electrode allows a complete circuit to be formed which will enable standard techniques in the art, such as amperometric measurements, to be performed using the chip. An electrode potential applied to the working electrode, where the electrochemically active materials are present through association with the capture probes and tag sequences, will produce current proportional to the amount of tag sequence attached to the capture probes.

Hybridization of the Double-Stranded DNA to a Chip

In some embodiments of the present invention, the double-stranded DNA molecule is a target for on-chip detection methods. For example, the target can be a PCR product that has been generated using a first strand primer having uracil in place of at least one thymine. Destabilization of hybridization in the region of this primer produces a first 5' flap sequence and a complementary exposed sequence on the second strand to which an exogenous polynucleotide can bind. In some embodiments of the present invention, the exogenous polynucleotide is a capture probe that is coupled to a surface or solid support. In some embodiments, the capture probe is coupled to a detection zone on a chip. The capture probe can be any sequence that is complementary to at least a portion of the exposed region of the second strand of the double-stranded DNA. For example, the capture probe can be a gene-specific sequence that is complementary to at least a portion of the exposed region of a specific target DNA. In certain embodiments, the probe comprises a sequence that is complementary to a tag sequence, such as an address tag, which is present in the exposed region of the target DNA. In such embodiments, the first 5' flap sequence of the double-stranded DNA comprises a sequence that is complementary to the tag sequence. As a result, the exposed region of the second strand, which becomes free for probe binding upon incubation of the duplex DNA with uracil-DNA glycosylase, comprises a nucleotide sequence that is complementary with the at least a portion of the capture probe. (FIG. 1) Accordingly, the double-stranded target DNA can be fixed to the surface comprising the capture probe.

Amplification Tags

In embodiments where the target DNA is hybridized to a gene-specific capture probe, the target DNA can be directly amplified and/or directly detected using on-chip amplification and/or detection methods. Some embodiment, however, use a universal capture probe that comprises a sequence complementary to an address tag which is identically present in the DNAs in the sample population. In such embodiments, all the double-stranded DNAs comprising the address tag will hybridize to the chip. Accordingly, the specific target sequence of interest should be identified then selected for on-chip amplification and/or detection. For example, the specific target DNA of interest can be identified by hybridization of its free end (the exposed region of the 3' end of the first strand) with a gene-specific nucleic acid probe. In such embodiments, the free end of the double-stranded target DNA comprises gene specific-sequence. The second strand primer, which has uracil in place of at least one thymine, is destabilized using uracil-DNA glycosylase, thereby generating a second 5' flap sequence. The exposed region of the first strand, which is complementary to the second 5' flap sequence, is free to bind to a gene-specific probe. In some embodiments of the present invention, the gene-specific probe comprises an amplification tag and/or a detection tag, which permits further hybridization with amplification probes and/or detection probes at the tag sequence.

On-Chip Amplification

A technique for enhancing the signal of a nucleic acid duplex on a chip is to amplify or extend the target nucleic acid after hybridization to the capture probe. The amplified or extended target nucleic acid can then be bound to a detector reagent (for example, a detection probe or a detector molecule). Preferably, the target strand is elongated so as to make the difference between the current at an unhybridized capture probe and the current at a probe/target duplex as profound as possible. This technique may be referred to as "on-chip amplification" and is disclosed in copending U.S. patent application Ser. No. 10/429,293, entitled METHOD OF ELECTROCHEMICAL DETECTION OF SOMATIC CELL MUTATIONS, filed May 2, 2003, the disclosure of which is incorporated herein by reference in its entirety.

Figure 2A:
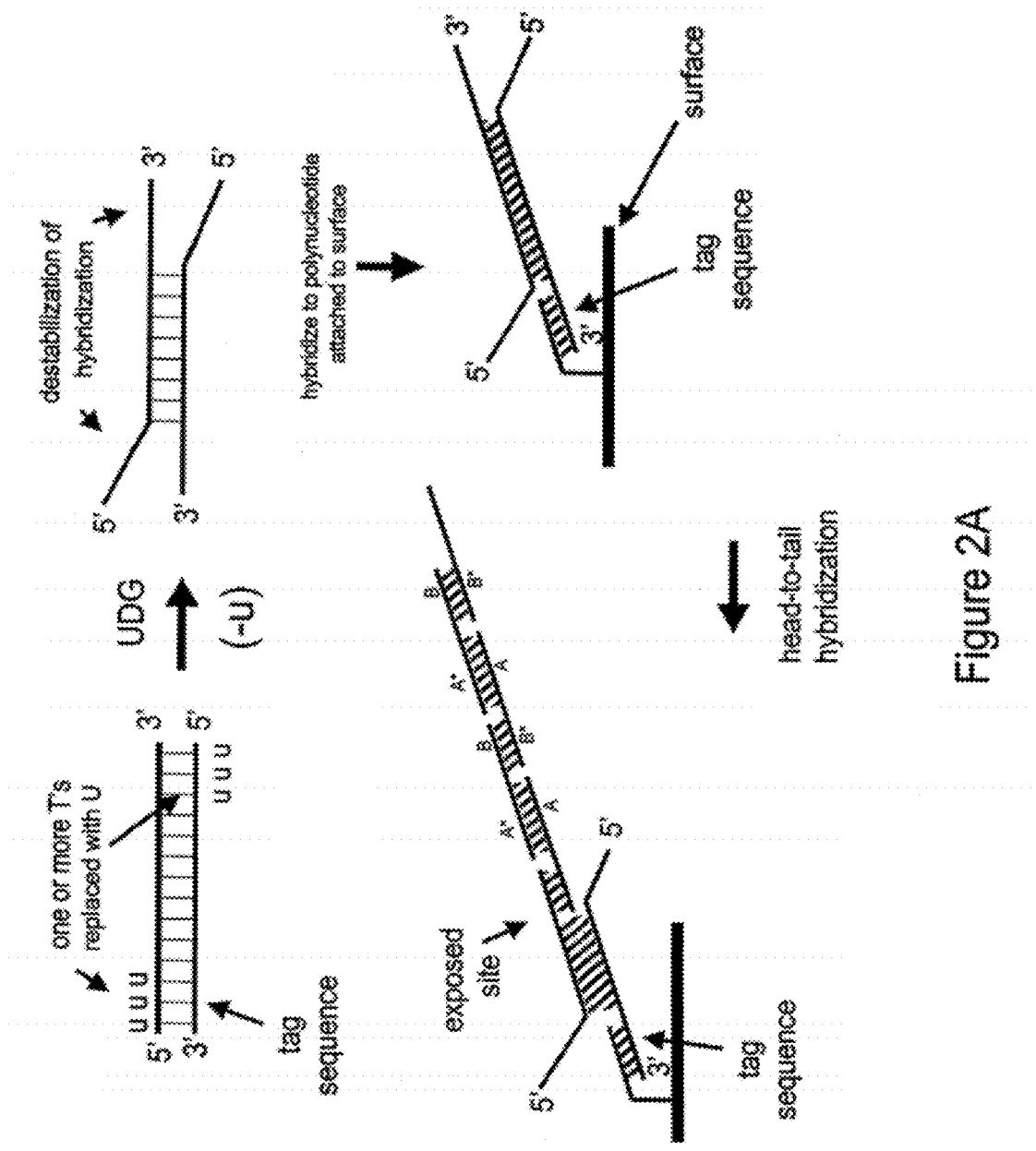
FIG. 2A illustrates destabilization of hybridization in regions at the ends of a linear double-stranded DNA using uracil-DNA glycosylase and subsequent hybridization of one end to a surface and the other end to a head-to-tail amplification probe.

Various methods of on-chip amplification can be used with the methods described herein. For example, head-to-tail polymerization, which is depicted in FIG. 2A, is one method of on-chip amplification that can be used with the destabilization methods described herein. In such methods, a free end of a hybridized target strand can be targeted for a head-to-tail polymerization that builds up the amount of DNA on the electrodes. Typically, three different oligonucleotides (not counting the immobilized probe and the target strands) will be used as shown here: the first oligomer is complementary to the 3' end of the hybridized target strand (targeting the complement of the primer sequence), and contains a sequence A at its 5' end; the second oligomer has a sequence 5'-A*B-3', where A* is complementary to A; the third oligonucleotide has sequence 5'-AB*-3'. As depicted in FIG. 2A, these oligomers can form a polymeric product as shown. The head-to-tail polymerization can continue until the strand reaches a desired length. Generally, when performing head-to-tail polymerization, the ultimate length of the polynucleotide is limited in part by a competing cyclization reaction of the head-to-tail oligomers. A higher concentration of head-to-tail oligomers in the liquid medium will generally produce longer linear polymers attached to the electrode, however.

Figure 2B:
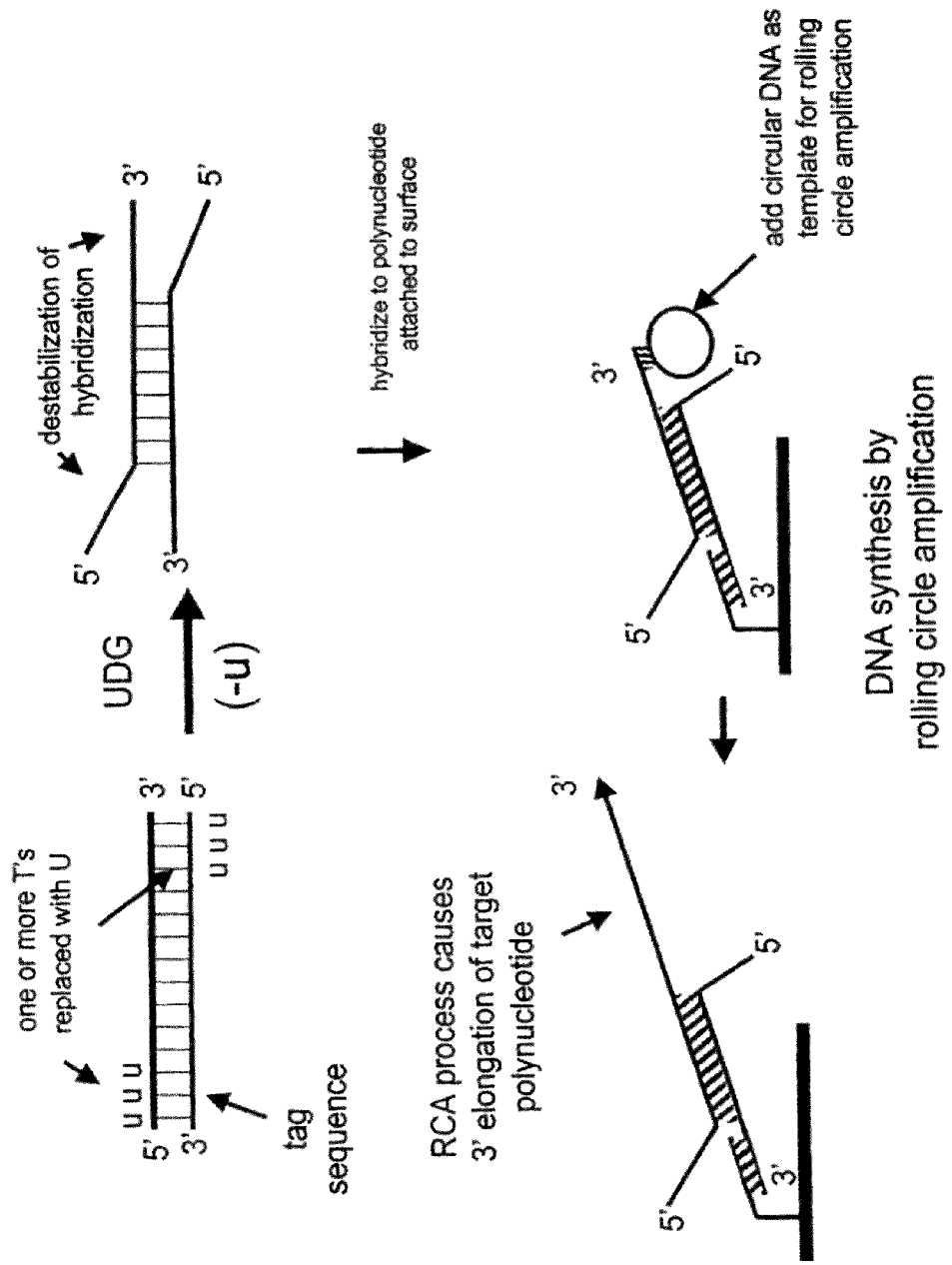
FIG. 2B illustrates destabilization of hybridization in regions at the ends of a linear double-stranded DNA using uracil-DNA glycosylase and subsequent hybridization of one end to a surface and the other end to an RCA template.

A second method of on-chip amplification is depicted in FIG. 2B. This method uses rolling circle amplification (RCA). Preferably, a preformed circle (approximately 40 to 300 nucleotides) that has a region complementary to the exposed region of the 3' end of the first strand of bound target DNA, or an amplification or elongation product produced therefrom, is hybridized to the target DNA that is hybridized to the capture probe. A processive DNA polymerase can then be added so that RCA results, elongating the bound target nucleic acid from the sample or amplification or elongation product produced therefrom. Preferably, the target nucleic acid from the sample is elongated by approximately 10 to 10,000 copies of the circle. Subsequent to the amplification, a detector reagent, such as a detection probe, a signal generating probe or detector molecule, can then be bound to the RCA product.

A further technique for on-chip amplification is depicted in FIG. 2C. This technique may be referred to as "bridge" amplification or "branch" amplification, as the terms "bridging" and "branching" are synonymous in this context. In this method, the exposed region of the target nucleic acid from the sample or an amplification or elongation product produced therefrom is hybridized to the capture probe. A first preformed circle is hybridized to the target nucleic acid from the sample or an amplification or elongation product produced therefrom, and RCA is performed to produce a first RCA product. A bridge nucleic acid comprising a sequence complementary to a sequence in the first RCA product and a sequence complementary to a sequence in a second preformed circle is provided. The bridge nucleic acid is hybridized to the first RCA product and a second RCA procedure is performed with the second preformed circle, thereby producing a second RCA product. A detector reagent is then bound to the target nucleic acid from the sample or amplification product or elongation product produced therefrom, first RCA product, bridge nucleic acid, second RCA product, or any two or more of the preceding nucleic acids. It will be appreciated that the first RCA procedure and/or the second RCA procedure may be substituted with head-to-tail polymerization or with another elongation procedure if desired. It will also be appreciated that rather than using a preformed circle for rolling circle amplification, a linear molecule containing sequences at each end which hybridize to the target nucleic acid or amplification or elongation product produced therefrom or to the bridge nucleic acid may be circulated after hybridization to generate a circular template for RCA.

Figure 2D:
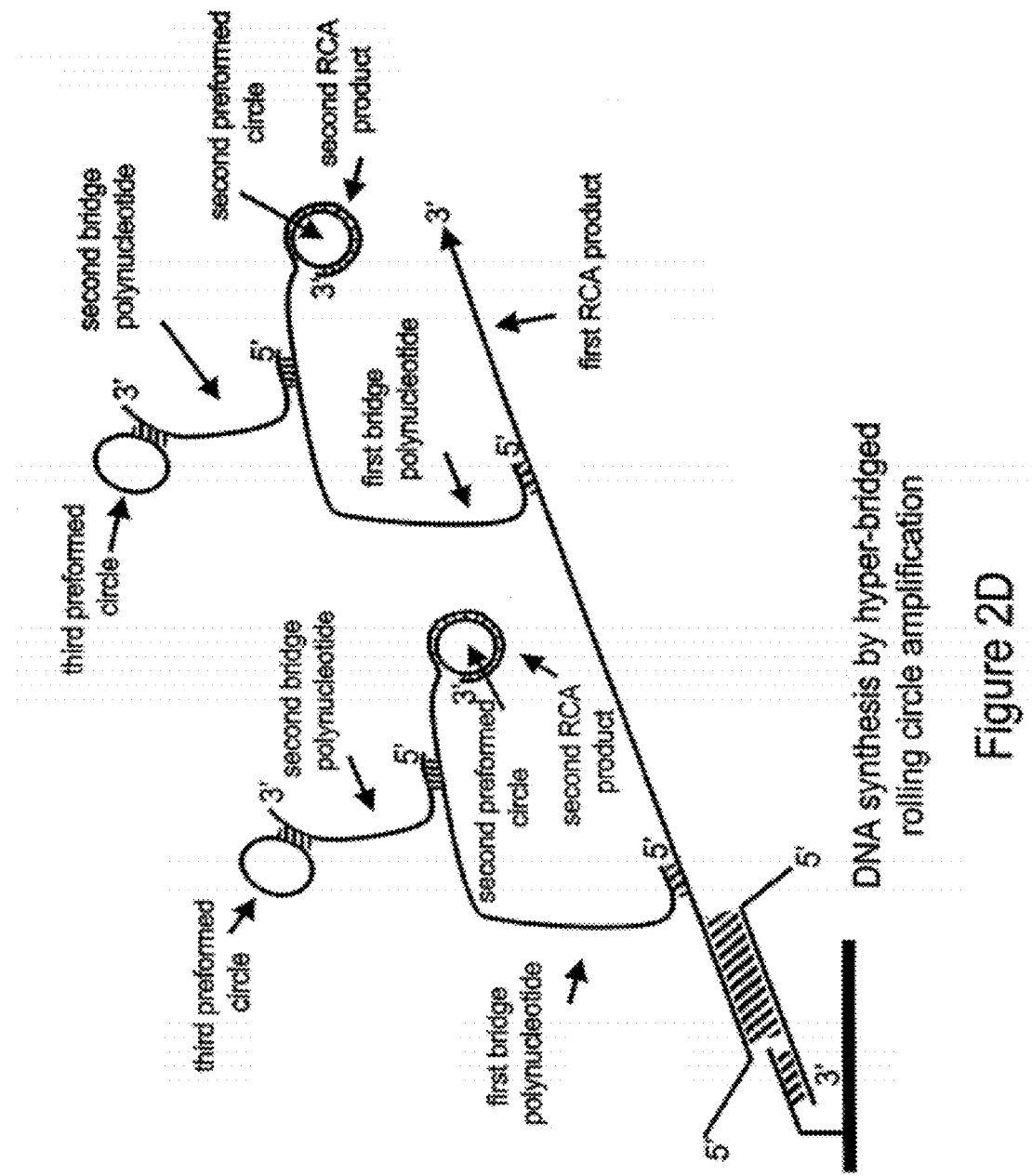
FIG. 2D illustrates destabilization of hybridization in regions at the ends of a linear double-stranded DNA using uracil-DNA glycosylase, subsequent hybridization of one end to a surface and extension of the other end by hyperbranched RCA.

Further, when a bridge amplification technique is used, it can be advantageous to increase the extent of branching using a technique known as "hyperbridging" or "hyperbranching." An example of hyperbridging is shown in FIG. 2D. Here, a second bridge nucleic acid comprising a sequence complementary to a sequence in the second RCA product and a sequence complementary to a sequence in a third preformed circle is provided. The second bridge nucleic acid is hybridized to the second RCA product and a third RCA procedure is performed with the third preformed circle, thereby producing a third RCA product. A detector reagent is then bound to the target nucleic acid from the sample or amplification or elongation product produced therefrom, first RCA product, first bridge nucleic acid, second RCA product, second bridge nucleic acid, third RCA product, or any two or more of the preceding nucleic acids. It will be appreciated that the first RCA procedure, second RCA procedure, third RCA procedure, or any combination thereof may be substituted with head-to-tail polymerization or with another elongation procedure if desired. It will also be appreciated that rather than using preformed circles in any of the RCA procedures, a linear molecule containing sequences at each end which hybridize to the target nucleic acid or amplification or elongation product produced therefrom to the first bridge nucleic acid, or to the second bridge nucleic acid may be circularized after hybridization to generate a circular template for RCA.

It is generally advantageous to use an elongation technique such as rolling circle amplification or head-to-tail polymerization in conjunction with a hyperbridging process. Elongation generally serves the purpose of adding nucleic acid material that can be detected electrochemically to help distinguish hybridized from unhybridized nucleic acids, but the process can also be beneficial since longer nucleic acids provide more locations in which additional bridges can be attached.

Bridging and hyperbridging can be particularly useful techniques since the amount of nucleic acid present can be increased exponentially. Additional discussion of bridging and hyperbridging techniques can be found, for example, in: Urdea, Biotechnology 12:926 (1994); Horn et al., Nucleic Acids Res. 25(23):4835-4841 (1997); Lizardi et al., *Nature Genetics* 19, 225-232 (1998); Kingsmore et al. (U.S. Pat. No. 6,291,187); Lizardi et al. (PCT application WO 97/19193); all of which are hereby incorporated by reference.

When performing an assay that includes on-chip amplification, it is possible to detect hybridization with or without using a bridging step. Assuming that a detection probe is used to associate a redox enzyme with hybridized nucleic acid, the following two examples outline steps that could be taken in an assay that does not feature bridging, and an assay that does feature bridging respectively.

A method without bridging generally includes the following steps: 1) (optional) determine specificity through ligation 2) bind the target to the probe; 3) perform RCA on the bound target; 4) add a detection probe containing an epitope, such as fluorescein; add an antibody linked to a redox moiety such that the antibody is capable of binding to the epitope; 5) detect the redox activity related to the presence of the redox moiety.

A method that features a bridging step generally includes the following: 1) (optional) determine specificity through ligation 2) bind the target to the probe; 3) perform RCA on the bound target; 4) add a bridge nucleic acid and a second circle; 5) perform RCA at the bridge; 6) add a detection probe which hybridizes to the RCA product containing an epitope, such as fluorescein; 7) add an antibody linked to a redox moiety such that the antibody is capable of binding to the epitope; 8) Detect the redox activity related to the presence of the redox moiety.

After performing an on-chip amplification, the increased amount of DNA can generate a larger and more detectable signal. This can be advantageous for assay purposes since both the probe and the target typically produce some detectable signal. If the signal of the target is enhanced, the contrast between hybridized and unhybridized capture probes will be more profound. In some embodiments, however, nucleic acid analogs such as methyl phosphonates and PNAs can be used as capture probes. In other embodiments, nucleic acid analogs such as methyl phosphonates and PNAs can be used as detection probes. Accordingly, on-chip amplification of nucleic acid is a versatile useful technique for enhancing the signal of hybridized target.

On-chip amplification can be used alone, or in conjunction with other signal enhancing techniques such as catalytic detection. Some embodiments include the steps of: (1) hybridizing the exposed region of a target to a capture probe immobilized on an electrode surface; (2) performing on-chip rolling circle amplification using a polymerase with high processivity and strand displacement capability; (3) binding a detection probe to the amplified product on the chip; and (4) detecting catalytic signal generated from a highly electrochemically reactive enzyme.

In some embodiments of the present invention, horseradish peroxidase (HRP) is used in generate electrons by the redox conversion of hydrogen peroxide to water. HRP is particularly useful as a detector reagent because of its stability, high turn over rate, and the availability of sensitive electrochemical mediators. Other enzymes such as phosphatases, other peroxidases including microperoxidase, and oxidases can also be used for this purpose. In some embodiments, the electrochemical detection using HRP proceeds as follows:

$$HRP_R + H_2O_2 + 2H^+ \rightarrow HRP_O + 2H_2O$$

$$HRP_O + Med_R \rightarrow HRP_R + Med_O$$

$$Med_O + ne^- \rightarrow Med_R$$

Wherein Med denotes an electron transfer mediator that shuttles electrons between the enzyme and the electrode surface. Useful mediators include tetramethylbenzidine (TMB) and ferrocene derivatives. It will be appreciated by those of skill in the art that other enzymes, particularly other peroxidases can be used instead of HRP, and that other electron transfer mediators can be used instead of TMB.

Nucleic Acid Detection Methods

Numerous methods for detecting hybridized nucleic acids are available. For example, detection methods having increased sensitivity are described in U.S. Provisional Patent Application entitled NUCLEIC ACID DETECTION METHOD HAVING INCREASED SENSITIVITY, Ser. No. 60/518,816, the disclosure of which is incorporated herein by reference in its entirety. A non-exhaustive description of some of the available detection methods is set out below, however, it will be appreciated that any methods of nucleic acid detection that are known in the art can be used with the methods described herein.

Figure 2E:
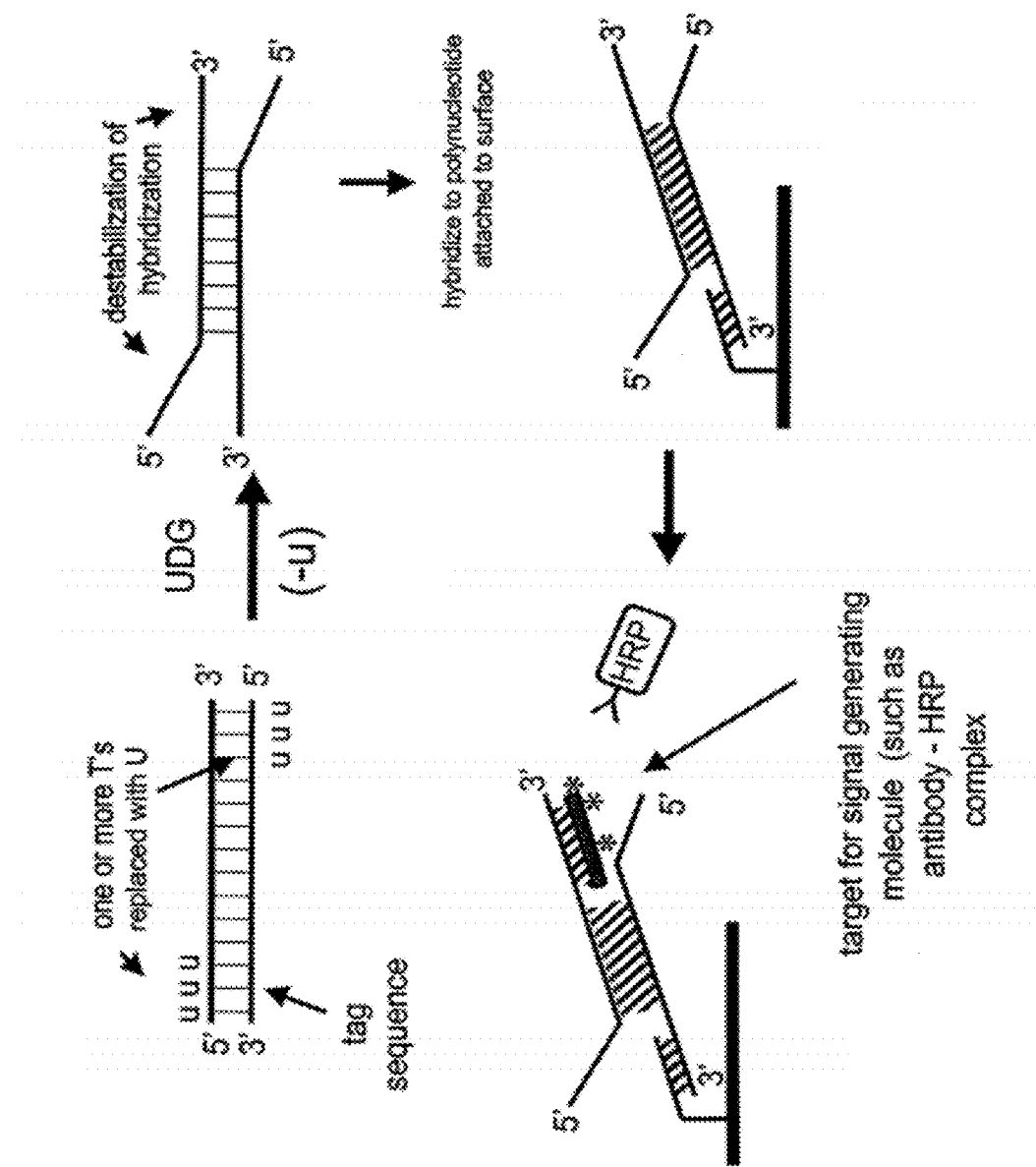
FIG. 2E illustrates destabilization of hybridization in regions at the ends of a linear double-stranded DNA using uracil-DNA glycosylase and subsequent hybridization of one end to a surface and the other end to a probe comprising a signal generating molecule.

The detection methods described herein can be applied to nucleic acids which have been amplified using on-chip amplification methods or can be applied directly to unamplified nucleic acids. In one embodiment, a bound unamplified nucleic acid is hybridized with a detection probe having one or more detector molecules included thereon (FIG. 2E). An antibody then binds specifically to the detector molecules and the signal is amplified using enzyme-linked secondary antibody. If the secondary antibody is conjugated to a redox enzyme, such as HRP, the signal can be detected using amperometry.

In some embodiments of the present invention, nucleic acid hybridization can be detected using a transition metal complex capable of oxidizing at least one oxidizable base in an oxidation-reduction reaction under conditions that cause an oxidation-reduction reaction between the transition metal complex and the oxidizable base, where the probe, target DNA or both contain at least one oxidizable base. The oxidation-reduction reaction indicating hybridization is detected by measuring electron transfer from each oxidized base, as disclosed in U.S. Pat. No. 5,871,981, the disclose of which is incorporate by reference in its entirety.

In another embodiment, target DNAs bound by capture probes that are immobilized on gold or other electrodes may be carried out using methods disclosed by Steele et al. (1998, *Anal. Chem.* 70:4670-4677), the disclosure of which is incorporated herein by reference in its entirety. In certain other embodiments, hybridization of amplification probes to target DNAs bound by capture probes that are immobilized on gold or other electrodes are contemplated. For example, multivalent ions with 2, 3, or 4 positive charges are used, which are capable of electrochemical detection by direct reaction without affecting the nucleic acid. In some embodiments these ions bind electrostatically to nucleic acid phosphate irrespective of whether it is in the double-helical or single-stranded form. The presence or absence of an amplified hybridized sequence is determined for each capture probe, based on electron transfer measurements taken at each capture probe site. In some embodiments, double-stranded target DNA can be contacted with the oligonucleotide capture probe using the strand destabilization methods described herein. By way of example, a double-stranded target DNA sample can be in solution and the oligonucleotide capture probes immobilized on a solid support, whereby the target DNA sample comprising at least one uracil is contacted with the oligonucleotide capture probe by immersing the solid support having the oligonucleotide capture probes immobilized thereon in the solution containing the target DNA sample. After gene-specific amplification, suitable transition metal complexes that bind nucleic acid electrostatically are used to generate a detection current that is proportional to the length of the hybridized DNA complexes bound to the chip. Transition metal complexes whose reduction or oxidation is electrochemically detectable in an appropriate voltage regime include $Ru(NH_3)_6^{3+}$, $Ru(NH_3)_5pyridine^{3+}$ and other transition metal complexes that can be determined by one of skill in the art.

According to one embodiment of the present invention, oligonucleotide capture probe sequences may be designed to be redox inactive, or to have very low redox activity, for example as disclosed in U.S. Pat. No. 5,871,918, the disclosure of which is incorporated herein by reference in its entirety.

The occurrence of the oxidation-reduction reaction may be detected according to any suitable means known to those skilled in the art. For example, the oxidation-reduction reaction may be detected using a detection electrode to observe a change in the electronic signal which is indicative of the occurrence of the oxidation-reduction reaction. Suitable reference electrodes will also be known in the art and include, for example, silver, silver/silver chloride electrodes. The electronic signal associated with the oxidation-reduction reaction permits the determination of the presence or absence of hybridized tags by measuring the Faradaic current or total charge associated with the occurrence of the oxidation-reduction reaction. The current depends on the presence of the positively charged redox ion closely associated with the electrode, which in turn depends on the amount of nucleic acid phosphate hybridized to the electrode. The electronic signal may be characteristic of any electrochemical method, including cyclic voltammetry, normal pulse voltammetry, differential pulse voltammetry, chronoamperometry, and square-wave voltammetry. The amount of hybridized DNA is determined by subtracting the current or total charge characteristic of the probes and other molecules bound to the electrode in the starting state from the current or total charge measured after the hybridization reaction.

Additional methods for the detection of target nucleic acids have been described in U.S. Provisional Patent Application No. 60/488,177, entitled INVASIVE CLEAVAGE REACTION WITH ELECTROCHEMICAL READOUT, filed Jul. 16, 2003; U.S. Provisional Patent Application No. 60/497,821, entitled OLIGONUCLEOTIDE SEQUESTERING AGENTS AND METHODS OF USE, filed Aug. 25, 2003 and U.S. Provisional Patent Application entitled NUCLEIC ACID DETECTION METHOD HAVING INCREASED SENSITIVITY, Ser. No. 60/518,816, the disclosures of which are incorporated herein by reference in their entireties.

Universal Tag Assays

Some aspects of the method described herein can be applied to a detection methods such as the Universal Tag Assay. The use of identifier tags for determining the presence or absence of a specific target nucleic acid in a sample has been described in copending U.S. patent application Ser. No. 10/424,543, entitled UNIVERSAL TAG ASSAY, filed Apr. 24, 2003, the disclosure of which is incorporated herein by reference in its entirety.

Formation of Single-Stranded Circular DNA

Figure 3:
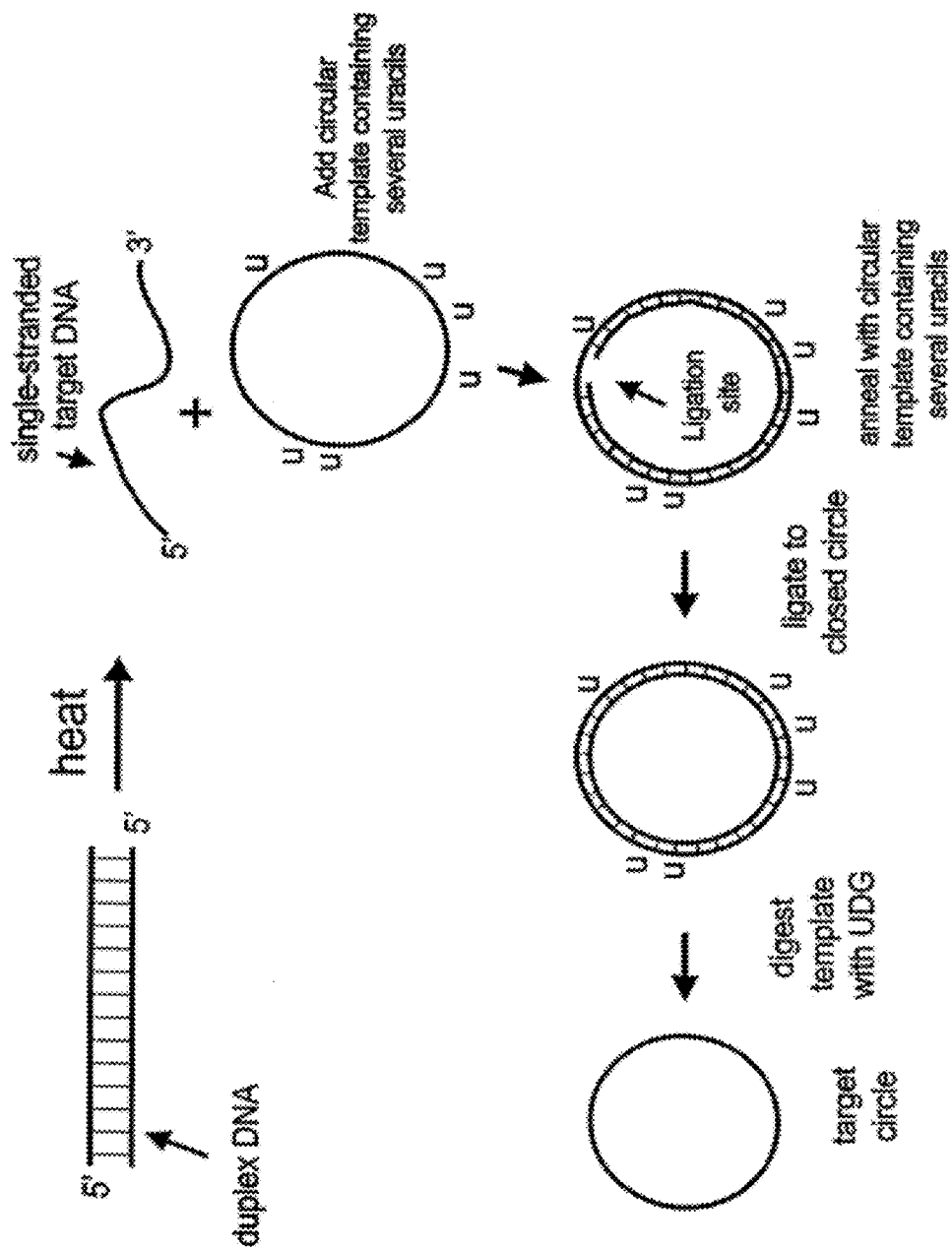
FIG. 3 illustrates the conversion of a double-stranded linear DNA to a single-stranded circular DNA using uracil-DNA glycosylase.
Figure 4:
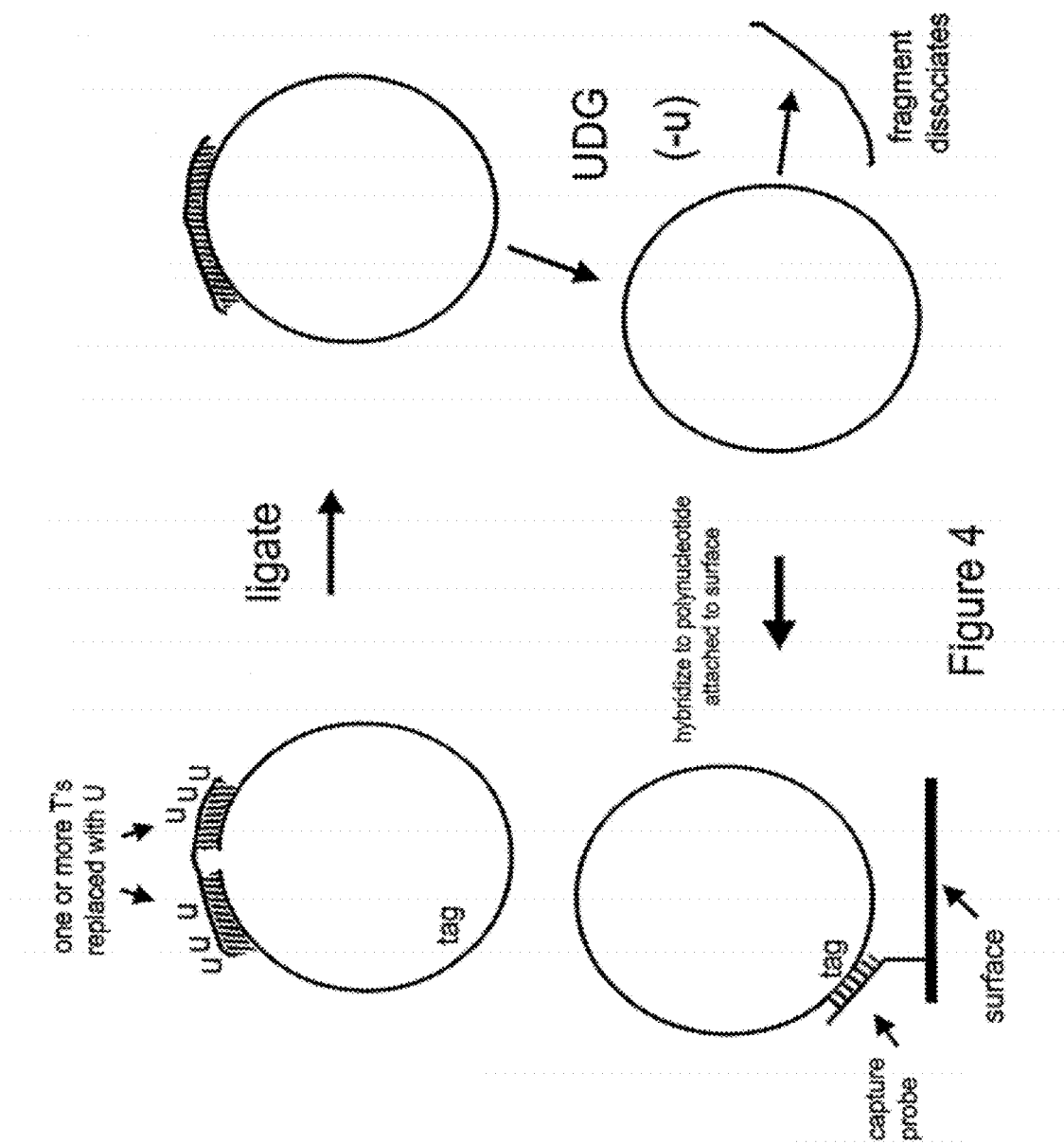
FIG. 4 illustrates the conversion of a single-stranded linear DNA to a single-stranded circular DNA using uracil-DNA glycosylase.

Some embodiments of the present invention relate to the formation of a circular single-stranded DNA. In some embodiments, a linear DNA is converted into a single-stranded circular DNA using the destabilization methods described herein. For example, a template DNA is synthesized such that uracil replaces thymine throughout the template. A single-stranded linear DNA is hybridized with a template DNA such that the 5'-end and the 3'-end of the single-stranded linear DNA are positioned adjacent each other thereby permitting formation of a phosphodiester bond between the 5' phosphate and the free 3' hydroxyl. In some embodiments, the template is a circular DNA. (FIG. 3). In other embodiments, the template is an oligonucleotide having a 5' portion that is complementary to the 3' portion of the linear strand. (FIG. 4). The 5' portion of the template is directly adjacent a 3' portion that is complementary to the 5' portion of the linear strand. Thus, hybridization of the linear strand with the template brings the 5' and 3' ends of the linear strand immediately adjacent each other. After ligation to seal the circle, the double-stranded DNA is incubated with uracil-DNA glycosylase and heated or treated with AP-endonuclease, which destabilizes hybridization between the template DNA and the resulting circular strand, thereby releasing the single-stranded circular DNA. (FIGS. 3 and 4).

Kits

Some aspects of the present invention also contemplate a kit for destabilizing hybridization of a DNA duplex. Some embodiments of the kits contemplated herein contain a DNA N-glycosylase, such as uracil-DNA glycosylase. In some embodiments, the kits also comprise an AP-endonuclease. The DNA N-glycosylase and AP-endonuclease can be provided in any convenient form including, but not limited to, in solution, frozen or lyophilized. In some embodiments of the present invention, kits also optionally include instructions for using the DNA N-glycosylase and, if present, the AP-endonuclease to destabilize hybridization between two DNA strands.

Other embodiments of the kits additionally comprise a chip having a plurality of capture probes attached thereto. In some embodiments, the chips can comprise an array of capture probes. In other embodiments, the capture probes each comprise one or more sequences complementary to an address tag. Arrays of capture probes comprising sequences complementary to address tags of different length and sequence are also contemplated. Such kits are useful for multiplexed DNA analysis. Still other embodiments of kits also include primers that are complementary to at least a portion of a desired target DNA.

One of ordinary skill in the art will recognize that the methods described and exemplified herein which relate to the use of uracil DNA N-glycosylase and AP-endonuclease to destabilize DNA hybrids having thymines replaced with uracils can be implemented using alternate enzymes having DNA N-glycosylase activity in combination with other non-natural DNA bases.

Some embodiments of this invention are further illustrated by the following examples which should not be construed as limiting. It will be appreciated by those of skill in the art that the techniques disclosed in the examples which follow represent techniques discovered by the inventor to function well in the practice of the embodiments of the invention described herein, and thus can be considered to constitute preferred modes for the practice of these embodiments. Those of skill in the art will, however, in light of the present disclosure, appreciate that many changes can be made in the specific embodiments which are disclosed herein and still obtain a like or similar result without departing from the spirit and scope of the invention.

EXAMPLES

Example 1

Synthesis of a Single-Stranded Template Having Uracil in Place of Thymine

In this example, a single-stranded deoxyribonucleic acid is synthesized having uracil in place of thymine.

A 35 base oligonucleotide is designed such that its 5' portion (15 bases) comprises the same sequence as a capture probe having the sequence 5'-GTACGGATAACTACG-3' (SEQ ID NO: 1) except the thymines are replaced with uracils as follows: 5'-GUACGGAUAACUACG-3' (SEQ ID NO: 2). The remaining 3' portion of the oligonucleotide (20 bases) is complementary to a portion of human genomic DNA having Coriell accession number NA12444B, incorporated herein by reference in its entirety, and does not comprise uracil. The 40-mer single-stranded DNA is synthesized using standard phosphoramidite chemistry with dU-phosphoramidite on an ABI 394 nucleic acid synthesizer.

In the next example, a double-stranded deoxynucleic acid is synthesized having uracil in place of thymine at the 5' end of each strand

Example 2

Generation of a Double-Stranded DNA Having Uracil in Place of Thymine

In this Example, PCR is used to amplify a double-stranded DNA having uracil in place of thymine at the 5' ends of each strand.

A 35 base reverse PCR primer is designed such that its 5' portion comprises the same sequence as a 15 base portion of the circular RCA probe 75.03 having the sequence 5'-CGTAGTTATCCGTAC-3' (SEQ ID NO: 3) except the thymines are replaced with uracils as follows: 5'-CGUAGUUAUCCGUAC-3' (SEQ ID NO: 4). The remaining 3' portion of the primer (20 bases) is complementary to a portion of human genomic DNA having accession number NA12444B (Coriell) and does not comprise uracil. The 35-mer reverse PCR primer is synthesized using standard phosphoramidite chemistry with dU-phosphoramidite on an ABI 394 nucleic acid synthesizer. The forward primer is the uracil-containing 35-mer from Example 1.

The reverse PCR primer is used together with the forward PCR primer to amplify a portion of human genomic DNA. The amplification product has a first strand that comprises the uracil-containing forward primer at its 5' end and a second strand which comprises the uracil-containing reverse primer at its 5' end.

The next Example describes the binding of this amplification product to capture probe.

Example 3

Binding and Detection of a Destabilized Double-Stranded Target DNA to a Capture Probe This Example demonstrates the destabilization of hybridization in the 5' regions of the PCR amplification product synthesized in Example 2 and subsequent binding to a capture probe.

An oligonucleotide comprising the sequence 5'-GTACGGATAACTACG-3' (SEQ ID NO: 1), to be fixed to the surface of a universal chip for use as a detection probe, is dissolved to a final concentration of 6 µM in a buffer comprising 10 mM HEPS, 50 mM LiCl and 0.4 mg/ml NeutraAvidin at pH 7.4. After 20 minutes the solution is adjusted to contain 12.5% isopropanol and 6 µl of the solution was deposited onto a universal detector chip. The chip is dried at room temperature, coated with Stable coat for 20 minutes, and then dried in a vacuum. To remove any unbound detection probe, the chip is soaked at 37° C. in a solution of 10 mM HEPS, 200 mM LiCl and 0.05% Tween 20 at pH 7.5 for 15 minutes then rinsed twice with a solution of 10 mM HEPS and 10 mM NaCl at pH 7.4.

The PCR amplification product from Example 2 is incubated with 2 units of uracil-DNA glycosylase (New England Biolabs) at 37° C. for 45 minutes, heated to 50° C. for 15 minutes and then 95° C. for 15 minutes. The destabilized PCR product is then added to the above-described chip having the capture probe comprising SEQ ID NO: 1 bound thereto. The chip is then incubated 37° C. for 30 minutes. Following the incubation, the chip is washed with a buffer of 10 mM HEPS, 233 mM LiCl and 0.05% Tween 20 at pH 7.4 then rinsed with a buffer of 10 mM HEPS supplemented with 200 mM NaCl at pH 7.4. Both the wash and rinse steps are repeated.

Following the hybridization and washing steps, the chip is further incubated with a ruthenium detection solution containing 5 µM $Ru(NH_3)_6^{3+}$, 10 mM Tris and 10 mM NaCl at pH 7.4. After a final washing to remove excess detection solution, binding of ruthenium to DNA is measured using amperometry.

The next example is an experiment which utilizes methods similar to those described in Examples 1-3.

Example 4

Detection of Alleles at Two Loci

This example describes detection of alleles at two loci in a human genomic DNA sample using methods similar to those described in Examples 1-3.

Allele-specific amplification of portions of genomic DNA Accession No. NA12444B (Coriell) was performed using methods similar to those described in Examples 1-2. The portions of the genomic DNA that were amplified correspond to two gene loci (711 and 1717) each of which has a major allele and a minor allele. The genomic DNA (Accession No. NA12444B) was from an individual who is homozygous for the major allele at the two amplified loci.

Figure 5:
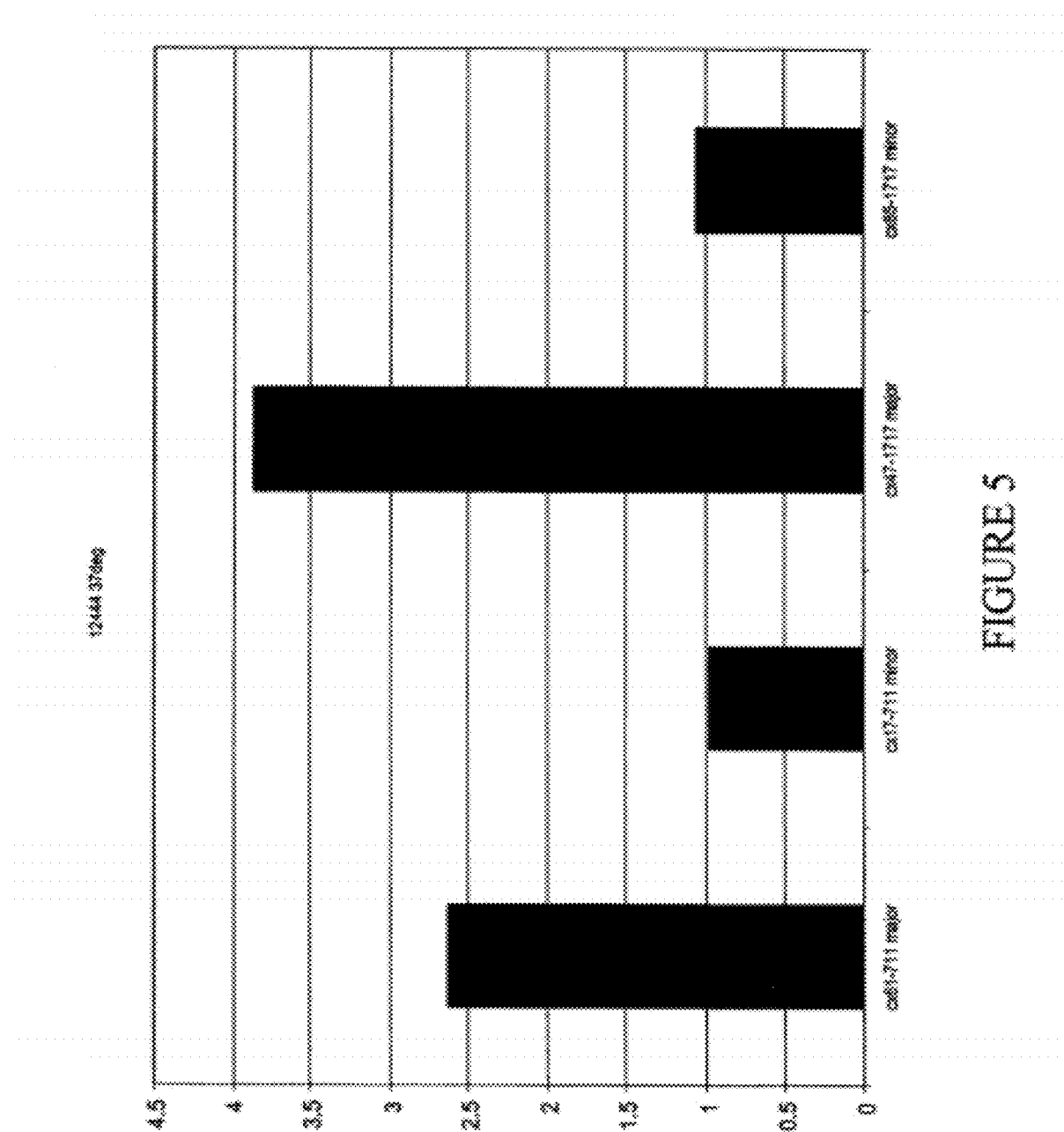
FIG. 5 is a chart showing the ratio of post-hybridization signal to pre-hybridization signal for the major and minor alleles for gene loci 711 and 1717.

Homozygosity of the individual was demonstrated by binding the amplification products for loci 711 and 1717 to a chip and detecting their presence using methods similar to those described in Example 3. Binding to the chip was allele-specific because each allele was tagged with an unique identifier tag during PCR amplification. Prior to hybridization, background signal was determined amperometrically (pre-hybridization signal). After hybridization, amplification and incubation with the detector reagent, signal was again measured (post-hybridization signal). FIG. 5 is a chart showing the ratio of post-hybridization signal to pre-hybridization signal for the major and minor alleles for gene loci 711 and 1717. For both loci, the ratio of post-hybridization signal to pre-hybridization signal for the major alleles is greater than 1 indicating a change in signal intensity subsequent to hybridization. The ratio of post-hybridization signal to pre-hybridization signal is 1 for both of the minor alleles indicating no change in signal intensity. These results demonstrate that only the major was detected, and thus, the individual is homozygous for loci 711 and 1717.

The next Example describes RCA amplification and detection of the bound PCR product.

Example 5

Amplification of Target DNA and Detection Using a POD Antibody Conjugate

This Example describes a method for amplifying the bound PCR product using RCA then detecting the signal using an antibody coupled to a peroxidase enzyme.

About 2.5 pM RCA probe 75.03 having the sequence 5'-GCCTGTCCAGGGATCTGCTCTTAC-CCTATAGTGAGTCGTATTACGTAGTTATCCG TAC-CAATACCTGTATTCCTT-3' (SEQ ID NO: 5) is dissolved in a buffer of 10 mM HEPS, 1 M LiCl and 0.05% Tween 20 and then transferred to the chip described in Example 3. The chip is incubated at 37° C. for 30 minutes. Following the incubation, the chip is washed with a buffer of 10 mM HEPS, 233 mM LiCl and 0.05% Tween 20 at pH 7.4 then rinsed with a buffer of 10 mM HEPS supplemented with 200 mM NaCl at pH 7.4. Both the wash and rinse steps are repeated.

RCA is performed by adding to the chip dNTPs and φ29 polymerase (New England Biolabs) dissolved in 029 polymerase buffer supplemented with 100 mM KCl. The RCA extension reaction is incubated for 1 hour at 37° C. then at room temperature for 30 minutes. The chip is washed twice with a buffer comprising 10 mM HEPS, 233 mM LiCl and 0.05% Tween 20 at pH 7.5 then rinsed with 10 mM Tris containing 200 mM NaCl.

For detection, the chip is incubated with 0.25 µM of a fluorescein containing signal probe T7-F2 having the sequence 5'-CCTATAGTGAGTCGT-3' (SEQ ID NO: 6) in a hybridization buffer comprising 10 mM Tris, 1 M NaCl, 0.05% Tween 20 and 0.05% bovine serum albumin (BSA). Hybridization occurs at 37° C. for 10 minutes then at room temperature for an additional 30 minutes. Following the hybridization, the chip is washed with PBS comprising 0.05% Tween 20. Next, the chip is incubated for 20 minutes at room temperature with a 1:200 dilution of antifluorescein antibody conjugated to peroxidase (POD) in PBS buffer comprising 0.5% casein and 0.05% Tween 20. The chip is then washed with PBS containing 0.05% Tween 20 and signal is detected using K-blue TMB.

The next Example describes head-to-tail amplification and detection of a bound PCR product using ruthenium.

Example 6

Head-to-Tail Amplification of Target DNA and Detection Using Ruthenium

This Example describes the binding of a destabilized PCR product to a chip, amplification using head-to-tail probes and detection by amperometry using ruthenium.

A PCR product is generated as described in Example 2 and then strand hybridization is destabilized at each end of the PCR product as described in Example 3. Subsequently, the destabilized PCR product is bound to a chip containing a complementary capture probe as described in Example 3.

After washing unbound PCR amplification product from the chip, single stranded head-to-tail probes AB and BA are added to the chip and incubated at 37° C. for 30 minutes to provide extension of the bound PCR product initiating from its exposed strand at the unbound end. Probe AB is a 30-mer which comprises the sequence 5'-AGGTCGATTGCCAT-GCGTAGTTATCCGTAC-3' (SEQ ID NO: 7). The 3' portion (15 bases) of probe AB is complementary to a portion of the exposed strand at the unbound end of the PCR product. Probe BA is a 30-mer which comprises the sequence 5'-CATG-GCAATCGACCTGTACGGATAACTACG-3' (SEQ ID NO: 8). The 5' portion (15 bases) of probe BA is complementary to the 5' portion (15 bases) of probe AB the 3' portion (15 bases) is complementary to the 3' portion of probe AB. As such, the added probes hybridize to each other in a head-to-tail fashion.

After hybridization of the head-to-tail probes, the chip is washed three times with a ruthenium detection solution containing 5 µM Ru(NH$_3$)$_6^{3+}$, 10 mM Tris and 10 mM NaCl at pH 7.4. Binding of ruthenium to DNA is measured using amperometry.

The next Example describes extension of the 3' end of a capture probe bound to a DNA template.

Example 7

Binding of a Double-Stranded Circle to a Capture Probe and Subsequent RCA

This Example describes binding of a circular RCA probe directly to a complementary capture probe, subsequent extension of the 3' end of the capture probe, and detection using ruthenium.

A single-stranded circular RCA probe having a sequence complementary to a capture probe is synthesized. A forward PCR primer having a nucleotide sequence corresponding to the sequence of the capture probe except that all thymines are replaced with uracils is synthesized as described in Example 1. The primer is mixed with the circular RCA probe and polymerization is initiated at the 3' end of the primer using Taq DNA polymerase, thereby generating a nicked double-stranded circular DNA (see FIG. 6).

The nicked double-stranded circular DNA is incubated with 2 units of uracil-DNA glycosylase (New England Biolabs) at 37° C. for 45 minutes, thereby generating a 5' flap region and exposing a region of the double-stranded circle that is complementary to a capture probe.

A chip having attached thereto a capture probe complementary to the exposed strand of the double-stranded RCA probe is prepared as described in Example 3. The destabilized double-stranded RCA probe is then incubated with the chip at 37° C. for 30 minutes. Following the incubation, the chip is washed with a buffer of 10 mM HEPS, 233 mM LiCl and 0.05% Tween 20 at pH 7.4 then rinsed with a buffer of 10 mM HEPS supplemented with 200 mM NaCl at pH 7.4. Both the wash and rinse steps are repeated.

RCA is performed by adding to the chip dNTPs and 029 polymerase (New England Biolabs) dissolved in φ29 polymerase buffer supplemented with 100 mM KCl. The RCA extension reaction is incubated for 1 hour at 37° C. then at room temperature for 30 minutes. The chip is washed twice with a buffer comprising 10 mM HEPS, 233 mM LiCl and 0.05% Tween 20 at pH 7.5 then rinsed with 10 mM Tris containing 200 mM NaCl.

Figure 6:
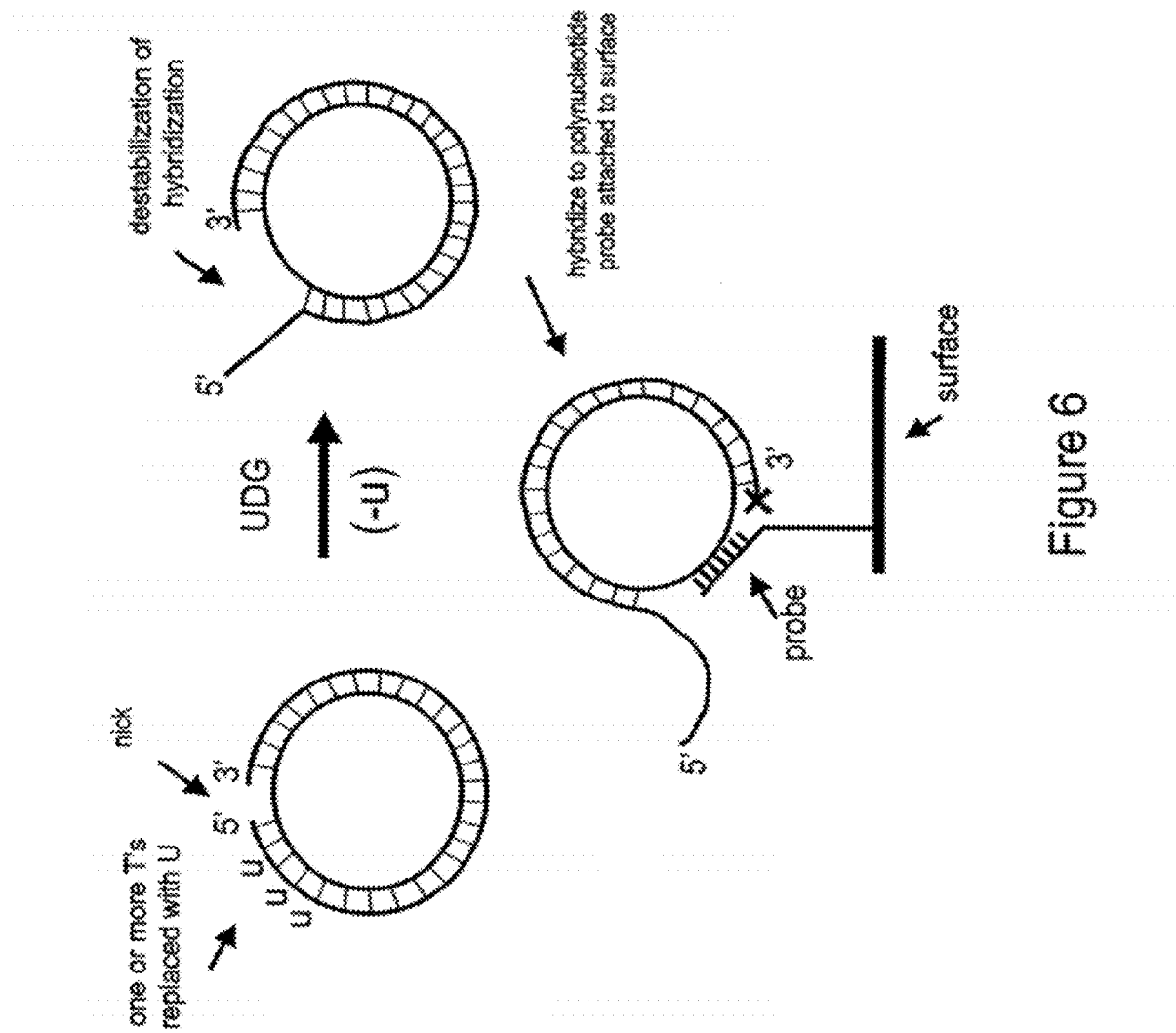
FIG. 6 illustrates destabilization of hybridization in a region of a double-stranded nicked-circular DNA using uracil-DNA glycosylase and subsequent hybridization to a probe coupled to a surface.

As shown in FIG. 6, RCA synthesis initiates at the 3' end of the capture probe but not at the 3' end of the nicked circular strand.

Example 8

Synthesis of a Single-Stranded Circular DNA Having an Exogenous Sequence

This example describes the use of a circular single-stranded uracil-containing DNA to generate a complementary single-stranded circular DNA having which includes an exogenous sequence.

Figure 7:
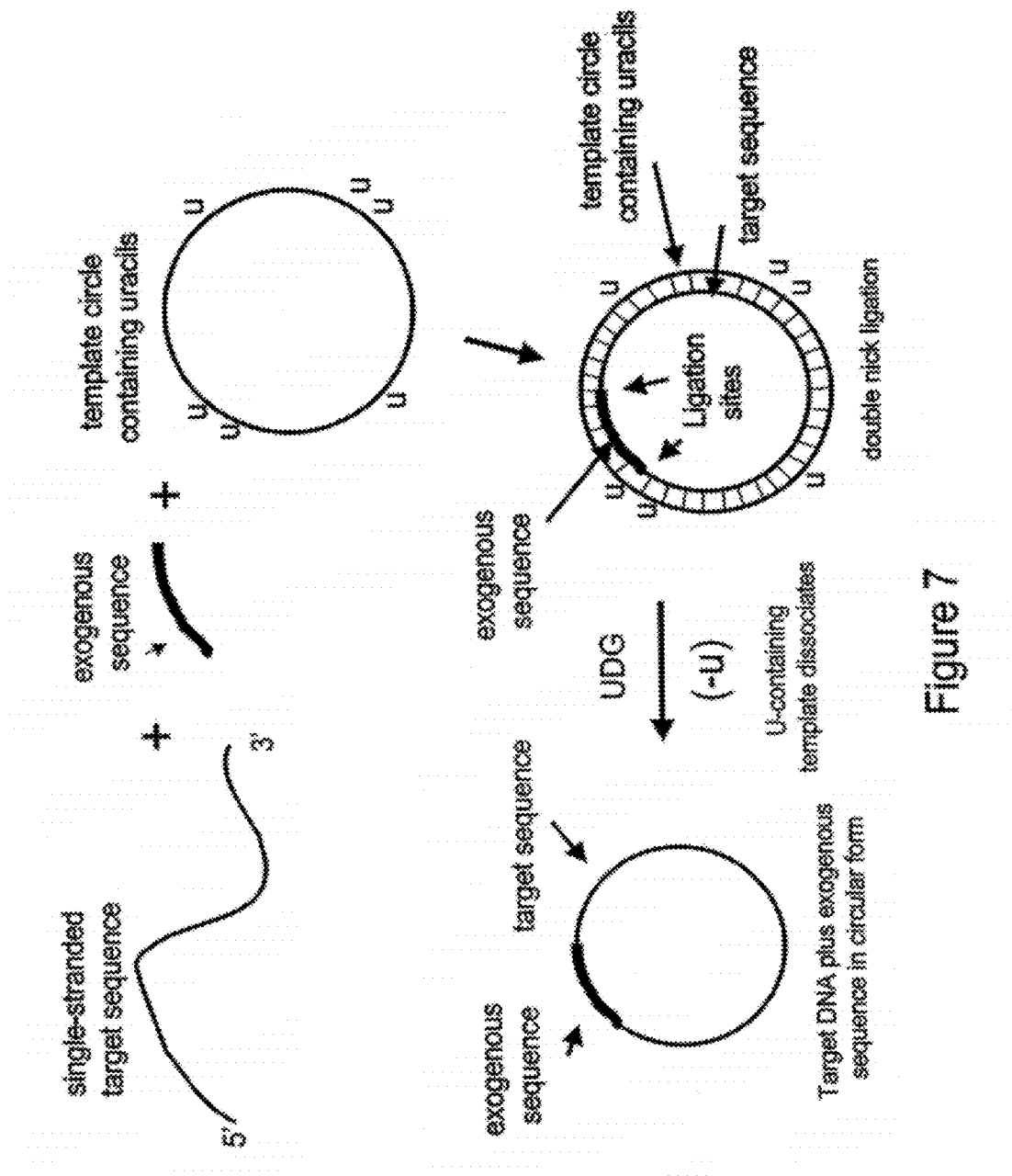
FIG. 7 the formation of a single-stranded circular DNA comprising an exogenous nucleotide sequence using uracil-DNA glycosylase.

A circular single-stranded DNA template is synthetically generated wherein all of the thymines have been replaced with uracils. To this template is added an equimolar amount of a linear single-stranded target DNA and a linear single-stranded exogenous DNA to be joined to the target strand as shown in FIG. 7. To this mixture is added 5 units of T4 DNA ligase to seal the nicks between the ends of the target DNA and the exogenous sequence thereby forming a relaxed double-stranded circular DNA.

To generate a free copy of the complementary single-stranded circular DNA, the reaction mixture is incubated with 2 units of uracil-DNA glycosylase (New England Biolabs) at 37° C. for 15 minutes. Five units of AP-endonuclease is then added and incubation is continued for an additional 15 minutes. The complementary circular DNA strand can be readily isolated by preparative gel electrophoresis.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of that which is described and claimed.

What is claimed is:

1. An array comprising:
a solid support comprising a capture probe; and
a double stranded nucleic acid comprising a first strand hybridized to second strand and at least one region where the hybridization of the first strand to the second strand is destabilized such that the first strand comprises a first unhybridized flap sequence and the second strand comprises a sequence complementary to the first flap sequence that is hybridized to the capture probe;
wherein said double stranded nucleic acid further comprises a second region where the hybridization of the first strand to the second strand is destabilized; and
wherein said second region is destabilized such that said second strand comprises a second unhybridized flap sequence and said first strand comprises a sequence complementary to the second flap sequence that is hybridized to a circular nucleic acid template.

2. The array of claim 1, wherein said first strand further comprises an extended region comprising a plurality of repeated sequences complementary to said circular nucleic acid template.

3. The array of claim 2, further comprising one or more bridge nucleic acids hybridized to said extended region.

4. The array of claim 3, wherein said one or more bridge nucleic acids further comprise an extended bridge sequence comprising a plurality of repeated sequences complementary to a second circular DNA template.

* * * * *

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
gtacggataa ctacg                                                    15

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 2
guacggauaa cuacg                                                    15

<210> SEQ ID NO 3
<211> LENGTH: 15
<212> TYPE: DNA
<213> ORGANISM: Artificial Sequence
<220> FEATURE:
<223> OTHER INFORMATION: PCR Primer

<400> SEQUENCE: 3
cgtagttatc cgtac                                                    15

<210> SEQ ID NO 4
<211> LENGTH: 15
<212> TYPE: DNA
<213> ORGANISM: Artificial Sequence
<220> FEATURE:
<223> OTHER INFORMATION: PCR primer

<400> SEQUENCE: 4
cguaguuauc cguac                                                    15

<210> SEQ ID NO 5
```

-continued

```
<211> LENGTH: 75
<212> TYPE: DNA
<213> ORGANISM: Artificial Sequence
<220> FEATURE:
<223> OTHER INFORMATION: RCA probe

<400> SEQUENCE: 5
gcctgtccag ggatctgctc ttaccctata gtgagtcgta ttacgtagtt atccgtacca      60
atacctgtat tcctt                                                      75

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
cctatagtga gtcgt                                                      15

<210> SEQ ID NO 7
<211> LENGTH: 30
<212> TYPE: DNA
<213> ORGANISM: Artificial Sequence
<220> FEATURE:
<223> OTHER INFORMATION: AB probe

<400> SEQUENCE: 7
aggtcgattg ccatgcgtag ttatccgtac                                      30

<210> SEQ ID NO 8
<211> LENGTH: 30
<212> TYPE: DNA
<213> ORGANISM: Artificial Sequence
<220> FEATURE:
<223> OTHER INFORMATION: BA probe

<400> SEQUENCE: 8
catggcaatc gacctgtacg gataactacg                                      30
```